(12) United States Patent
Xie et al.

(10) Patent No.: US 6,831,470 B2
(45) Date of Patent: Dec. 14, 2004

(54) METHODS AND APPARATUS FOR ESTIMATING ON-LINE WATER CONDUCTIVITY OF MULTIPHASE MIXTURES

(75) Inventors: Cheng-Gang Xie, Sawston (GB); Gerard Segeral, Gif sur Yvette (FR); Gilles Roux, Sainte Genevieve des Bois (FR); Paul Hammond, Bourn (GB)

(73) Assignee: Schlumberger Technology Corporation, Ridgefield, CT (US)

( * ) Notice: Subject to any disclaimer, the term of this patent is extended or adjusted under 35 U.S.C. 154(b) by 0 days.

(21) Appl. No.: 10/158,358

(22) Filed: May 30, 2002

(65) Prior Publication Data

US 2003/0011386 A1 Jan. 16, 2003

(30) Foreign Application Priority Data

May 30, 2001 (GB) .............................................. 0112973

(51) Int. Cl.$^7$ ......................... G01R 27/08; G01R 27/32
(52) U.S. Cl. ....................................... 324/693; 324/637
(58) Field of Search ................................ 324/439, 441, 324/442, 694, 691, 693, 633, 634, 637, 639–646; 73/152.08, 152.18

(56) References Cited

U.S. PATENT DOCUMENTS

| | | | |
|---|---|---|---|
| 4,233,839 A | * | 11/1980 | Coates ......................... 73/152 |
| 4,902,961 A | * | 2/1990 | De et al. ..................... 324/640 |
| 5,107,219 A | | 4/1992 | Marrelli et al. |
| 5,233,306 A | | 8/1993 | Misra |
| 5,272,444 A | | 12/1993 | Cox |
| 5,334,941 A | | 8/1994 | King |
| 5,341,100 A | | 8/1994 | Taylor |
| 5,676,259 A | | 10/1997 | Charchaflian et al. |

FOREIGN PATENT DOCUMENTS

| | | |
|---|---|---|
| GB | 2 313 196 | 11/1997 |
| GB | 2 349 227 | 10/2000 |
| WO | 99/42794 | 8/1999 |
| WO | 00/45133 | 8/2000 |

OTHER PUBLICATIONS

Hammer E A: "Flow permittivity models and their applications in multiphase meters", Proc. Multiphase Metering, IBC Technical Services, Mar. 12–13, 1997, Aberdeen.

Hammer E A: "Three component flow measurement in oil/gas/water mixtures using capacitance transducers", Ph.D. Thesis, UMIST, U.K., 1983.

Stogryn A, "Equations for calculating the dielectric constant of saline water", *IEEE Transactions on Microwave Theory and Techniques*, Aug. 1971, pp. 733–36.

Malmberg C G and Maryott A A, "Dielectric constant of water from 0° to 100°C", *Journal of Research National Bureau of Standards*, vol. 56, No. 1, Jan. 1956, RP2641.

Hilland J. "Simple sensor system for measuring the dielectric properties of saline solutions", *Meas. Sci. Technol.*, 8 (1997) 901–10.

Nörtemann K., Hilland J. and Kaatze U. "Dielectric properties of aqueous NaCl solutions at microwave frequencies", *J. Phys. Chem.* A, 101 (37) (1997) 6864–6869.

(List continued on next page.)

*Primary Examiner*—N. Le
*Assistant Examiner*—Amy He
(74) *Attorney, Agent, or Firm*—William L. Wang; William B. Batzer; John J. Ryberg

(57) ABSTRACT

A method and apparatus is disclosed for estimating brine water conductivity in a multiphase mixture of brine water and other substances by combining measured mixture permittivity and conductivity with a known or derived relationship between brine water conductivity and brine water permittivity. The mixture permittivity and conductivity are measured using an open-ended coaxial probe or other probes at microwave frequencies. A number of applications for the brine water conductivity estimate are disclosed including making salinity corrections of a dual energy flow meter.

35 Claims, 17 Drawing Sheets-

OTHER PUBLICATIONS

Friisø T., Schildberg Y., Rambeau O., Tjomsland T., Førdedal H. and Sjøblom J. "Complex permittivity of crude oils and solutions of heavy crude oil fractions", *J. Dispersion Sci. Technol.*, 19 (1) (1998) 93–126.

Tjomsland T., Hilland J., Christy A. A., Sjoblom J., Riis M., Friisø T. and Folgerø K., "Comparison of infrared and impedance spectra of petroleum fractions", *Fuel*, 75 (3) (1996) 322–332.

Folgerø K., Friisø T, Hilland J. and Tjomsland T. "A broad–band and high–sensitivity dielectric spectroscopy measurement system for quality determination of low–permittivity fluids", *Meas. Sci. Technol.*, 6 (1995) 995–1008.

Folgerø K. "Bilinear calibration of coaxial transmission and reflection cells for permittivity measurement of low–loss liquids", *Meas. Sci. Technol.*, 7 (1996) 1260–69.

Friisø T. and Tjomsland T. "Monitoring of density changes in low–permittivity liquids by microwave–permittivity measurements with an open–ended probe", *Meas. Sci. Technol.*, 8 (1997) 1295–1305.

Jakobsen T. and Folgerø K. "Dielectric measurement of gas hydrate formation in water–in–oil emulsions using open–ended coaxial probes", *Meas. Sci. Technol.*, 8(1997) 1006–15.

Folgerø K. and Tjomsland T. "Permittivity measurement of thin liquid film layers using open–ended coaxial probes", *Meas. Sci. Technol.*, 7 (1996) 1164–73.

Ellis D V: "Well Logging for Earth Scientists", Elsevier Science Publishing Co. 1987, Chapter 7.

"Wireline Formation Testing and Sampling", Schlumberger Wireline & Testing publication SMP–7058, 1996.

Marsland T P and Evans S. "Dielectric measurements with an open–ended coaxial probe." *IEE Proceedings* Pt.H, vol. 134, No. 4, Aug. 1997, 341–349.

A.M. Rowe and J.C.S. Chou (*Journal of Chemical and Engineering Data*, vol. 15, No. 1, 1970) "Pressure–Volume–Temperature–Concentration Relation of Aqueous NaCl Solutions".

Skre C D: "Water–in–liquid probe: system for measuring water–in–liquid ration at low and high gas volume fractions", Proc. $17^{th}$ Int. North Sea Flow Measurement Workshop, Clarion Oslo Airport Hotel, Gardermoen, Norway, Oct. 25–28, 1999.

Larson T A: "Operational experience and utilization of the data from the subsea multiphase flowmeter in the west brae field", North Sea Flow Measurement Workshop, Oct. 2000, Gleneagles, Scotland.

\* cited by examiner

METHODS AND APPARATUS FOR ESTIMATING ON-LINE WATER CONDUCTIVITY OF MULTIPHASE MIXTURES

FIELD OF THE INVENTION

The present invention relates to the field of multiphase flow measurement. In particular, the invention relates to a method and apparatus for estimating brine water conductivity of multiphase flow mixtures by interpreting mixture permittivity and mixture conductivity measured using a microwave open-ended coaxial reflection probe.

BACKGROUND OF THE INVENTION

To measure accurately the water fraction and the water-in-liquid ratio (WLR or water-cut) of oilfield oil-water-gas multiphase flows using electromagnetic sensors, it is greatly beneficial to know the brine conductivity which often varies with temperature, salinity and salt species (e.g. due to the water injection). For an electromagnetic water-cut monitor, water conductivity data is conventionally entered manually based on water sample analysis, or measured by flowing single-phase water through the sensing volume (however, the latter is often not possible under production conditions). Some multiphase flow meters utilize dual-energy gamma-ray principle to measure water-cut, with accuracy being highly dependent upon the calibrations of mass attentions of brine water as well as of oil and gas at line conditions. The brine mass attenuation at the lower photon energy is strongly dependent on the salinity and salt species; their departure from the initial calibration values as a water flood proceeds will result in erroneous water-cut and hence oil and water flow rates. Monitoring changes in water salinity on-line, under multiphase flow conditions, is thus highly desirable, especially for permanent (subsea) metering applications.

For characterizing materials in various industrial and scientific applications, open-ended electromagnetic coaxial probes have been used, based on the principle that the measured complex reflection coefficient (ratio of reflected signal to the incident) is dependent on the aperture impedance (thus complex permittivity) of a sample material terminating the probe. For such applications, commercial products are available such as Hewlett-Packard's 85070C Dielectric Probe Kit (for use with HP series of network analysers). To facilitate complex permittivity inversion, many aperture impedance models of coaxial probes have been developed, such as that disclosed in the U.S. Pat. No. 5,233,306.

The sensitivity depth of an open coaxial probe is shallow, about equal to the inner radius of the outer conductor of the probe (typically only a few millimeters). This means that the probe is sensitive to the bulk electrical property of a material in its close vicinity. In recent years, microwave open coaxial probes have been used in measuring the properties of single-phase and multiphase fluids encountered in oilfields. For example:

1. Complex permittivity of saline solutions (up to about 5 S/m), Hilland J. "Simple sensor system for measuring the dielectric properties of saline solutions", Meas. Sci. Technol., 8 (1997) 901–10; Nörtemann K., Hilland J. and Kaatze U. "Dielectric properties of aqueous NaCl solutions at microwave frequencies", J. Phys. Chem. A, 101 (37) (1997) 6864–6869.

2. Complex permittivity of crude oils and solutions of heavy oil fractions. See, e.g. Friisø et al., "Complex permittivity of crude oils and solutions of heavy crude oil fractions", J. Dispersion Sci. Technol., 19 (1) (1998) 93–126; Tjomsland et al., "Comparison of infrared and impedance spectra of petroleum fractions", Fuel, 75 (3) (1996) 322–332; Folgerø et al., "A broad-band and high-sensitivity dielectric spectroscopy measurement system for quality determination of low-permittivity fluids", Meas. Sci. Technol., 6 (1995) 995–1008; and Folgerø K., "Bilinear calibration of coaxial transmission and reflection cells for permittivity measurement of low-loss liquids", Meas. Sci. Technol., 7 (1996) 1260–69.

3. Monitoring density changes in low-permittivity hydrocarbons. See Friisø et al., "Monitoring of density changes in low-permittivity liquids by microwave-permittivity measurements with an open-ended probe", Meas. Sci. Technol., 8 (1997) 1295–1305.

4. Permittivity measurements of gas hydrate formation in water-oil emulsions. See, Jakobsen et al. "Dielectric measurement of gas hydrate formation in water-in-oil emulsions using open-ended coaxial probes", Meas. Sci. Technol.,8 (1997) 1006–15.

5. Permittivity of thin (water/oil) liquid layer backed by gas. See Folgerø et al., "Permittivity measurement of thin liquid film layers using open-ended coaxial probes", Meas. Sci. Technol., 7 (1996) 1164–73.

6. The water-cut measuring accuracy by using an open coaxial probe (flush mounted at pipe wall) has been demonstrated to be ±5% absolute with gas-cut up to 85%, given the oil and water permittivities (or conductivities). See Skre C D, "Water-in-liquid probe: system for measuring water-in-liquid ratio at low and high gas volume fractions", Proc. 17th Int. North Sea Flow Measurement Workshop, Clarion Oslo Airport Hotel, Gardermoen, Norway, 25–28 Oct. 1999. Beyond 85% gas-cut, the water-cut is underpredicted due to gas entrainment in the (oil-water) liquid layer close to the probe.

U.S. Pat. No. 5,341,100 discloses the use of a (four-port) coaxial transmission line for the (downhole) continuous measurement of water conductivity and hydrocarbon fraction under dynamic flow conditions. Formation fluid is directed to flow between the inner and the outer conductors of the coaxial structure (about 3" (7.6 cm) long). The permittivity and conductivity of the formation fluid are inferred from the phase-shift and attenuation of the transverse electromagnetic wave (TEM) measured between the near and far receivers (spaced along the flow tube with respect to a transmitter; a matched load is used to terminate a fourth port farthest from the transmitter). The operating frequency is kept low (about 100 MHz) to avoid large attenuation at high brine salinities and to eliminate measurement ambiguities due to the excessive phase-shift (>360°) between the receivers (1" (2.5 cm) spacing). Water conductivity and hydrocarbon fraction are determined from the fluid permittivity and conductivity; the interpretation scheme is not explicitly disclosed, but could be based on a look-up table approach. Additionally, the system hardware is rather complex.

U.S. Pat. No. 5,675,259 discloses the use of a single or multiple open-coaxial probes (operating at about 1 GHz), arranged almost non-intrusively (aperture flush mounted at pipe/vessel wall) or intrusively (e.g. mounted along the pipe diameter). By rapidly detecting amplitude and phase of the reflected signal, single-phase and multiphase fluids may be identified based on the differences between complex permittivities. Fluid flow rates may be measured by processing signals from probes mounted along a flow pipe. Different depths of investigation may be achieved by varying the intrusion length of the probe inner-conductor exposed to the fluid. However, estimating on-line water conductivity under multiphase conditions is not considered.

U.S. Pat. No. 5,272,444 describes the use of relatively low frequency (tens of MHz) dielectric (impedance) sensor for water-cut and salinity monitoring of water-oil flows, by cross-plotting two sensed parameters such as impedance (ratio) vs. phase, voltage vs. voltage measured at two frequencies. The cross-plot is used as a look-up table which is mapped over a range of water-cut, water resistivity and temperature.

PCT Patent Application No. WO 99/42794 discloses an open-coaxial probe of flat aperture surface (inner conductor not extending into fluid) for flush mount with inner pipe/tank wall (for placement at the liquid rich region even for vertical high-gas annular flows). The depth of investigation can be varied by changing the inner diameter of the outer conductor. To withstand high pressures and temperatures in oilfield tubings, the coaxial probe is designed to have a heat resistant plastic material (of low dielectric constant). To ensure a good seal between the inner and the outer conductors at the probe surface, a conical metal clamp is designed with screw adjustment pressing against a conical insulator (which in turn is pressed against the inner conductor).

SUMMARY OF THE INVENTION

Thus, it is an object of the present invention to provide a method of estimating water conductivity in a multiphase mixture of water and other substances comprising the steps of:
   obtaining values representing the mixture permittivity and mixture conductivity of the multiphase mixture;
   obtaining a relationship between water conductivity and water permittivity; and
   estimating water conductivity of the multiphase mixture using at least the values representing mixture permittivity, mixture conductivity, and the relationship between water conductivity and water permittivity.

The invention is also embodied in an apparatus for estimating water conductivity in a multiphase mixture of water and other substances comprising:
   one or more sensors for measuring mixture permittivity and mixture conductivity of the multiphase mixture; and
   a processor adapted to estimate water conductivity by combining the measured mixture permittivity and mixture conductivity with an obtained relationship between water conductivity and water permittivity.

As used herein the term "multiphase" means mixtures including multiple components such as oil-water, oil-water-gas, as well as water-solids, etc. When the term "conductivity" is used herein, it is understood that instead of conductivity one could use equivalents including for example the mathematical reciprocal "resistivity". The term "permittivity", as used herein, refers to a value relative to a vacuum, and is also commonly referred to as the dielectric constant. The terms "complex permittivity" as used herein refers to a complex value, with its real part mainly related to "permittivity" and its imaginary part to the permittivity loss (mainly the conductivity loss).

BRIEF DESCRIPTION OF THE DRAWINGS

FIG. 3b is longitudinal view of the coaxial probe 116 mounted in the spool piece shown in FIG. 3a;

FIG. 9b is a time series of the 10-Hz $\sigma_m(t)$ and $\in_m(t)$ data corresponding to FIG. 9a;

DETAILED DESCRIPTION OF THE INVENTION

Figure 1:
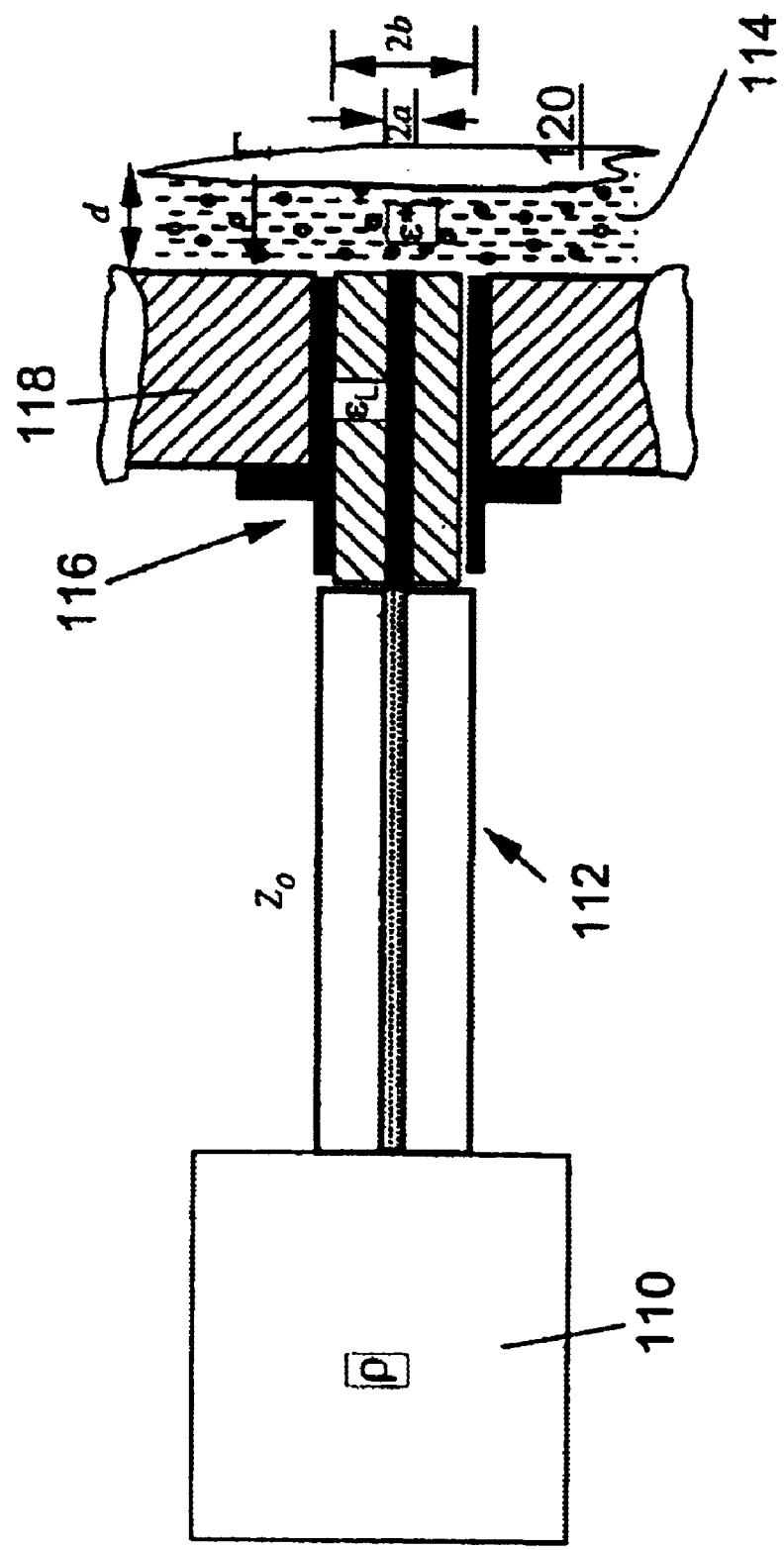
FIG. 1 shows a coaxial probe installed in a pipe wall, according to a preferred embodiment of the invention.

The following embodiments of the present invention will be described in the context of certain oilfield flow measurement arrangements, although those skilled in the art will recognize that the disclosed methods and structures are readily adaptable for broader application. Where the same reference numeral is repeated with respect to different figures, it refers to the corresponding structure in each such figure.

According to a preferred embodiment of the invention a single microwave open coaxial reflection probe is used for measuring water conductivity of dynamic oil/water/gas multiphase flow mixtures, by interpreting the simultaneously measured mixture permittivity ($\in_m$) and mixture conductivity ($\sigma_m$). For flows of sufficiently high water-cut (water continuous), when the water conductivity is fixed (for given salinity and temperature), the data points in the mixture conductivity and mixture permittivity parameter space tend to fall close to a distinct line connecting 100%-oil and 100%-water points. This is because, when water is rich, the mixture complex permittivity is dominated by the presence of water, whereas the gas and oil (hydrocarbon) have small and similar complex permittivities. It is also because hydrocarbon (gas and oil) volume fraction influences mixture permittivity and mixture conductivity in the similar way when water is continuous. This characteristic trend is unique to water-rich flows and the slope of the set of measured mixture conductivity vs. permittivity data points forms the basis for the on-line water-conductivity estimate. When flow mixtures become oil continuous and the water cut is relatively high, the instantaneous mixture conductivity-permittivity data points follows a predefined curve for each fixed water conductivity; by identifying this curve, on-line water-conductivity estimate is also provided.

The invention is also applicable to other microwave measurement techniques such as those based on transmission and resonance methods. The process of estimating water conductivity from the fundamental conductivity-permittivity parameter space (obtained from the appropriate transmission or resonance model) is essentially the same.

The on-line water conductivity measurement technique according to the present invention is applicable to many downhole applications, such as EPT (Electromagnetic Propagation Tool) salinity-independent water-saturation interpretation and improved on-line fluid discrimination and sampling for downhole fluid sampling techniques such as Schlumberger's Modular Formation Dynamics Tester (MDT).

The continuous liquid phase (oil or water) can also be determined (both mean mixture permittivity and mixture conductivity are at low values when oil is continuous). These two pieces of information can be used for providing other data, such as the determination of liquid mixture viscosity, useful for the accurate calculation of flow rate for venturi-based flow meters.

Other uses of on-line water conductivity (or salinity) estimation in multiphase mixtures for down-hole applications include:

1. The microwave open-coaxial probe can be used as a standalone salinity (and water-cut) meter, suitable for permanent monitoring and for produced water management (e.g. for detecting sweep water breakthrough, for managing the deployment of a down-hole water/oil separator).
2. The existing EPT (Electromagnetic Propagation Tool) gives estimate of water saturation of the invaded zone of a formation by interpreting the transmitting microwave attenuation and propagation time (mainly a function of receivers' phase-shift) through the zone. The interpretation of water saturation based on a permittivity mixing law (of the rock matrix and the pore fluids) could be more robust when using the fundamental parameters of the zone permittivity and/or conductivity, both being a function of the measured attenuation and phase shift. By interpreting these two parameters in a similar way according to the invention, water salinity in the invaded zone can also be obtained, thus yielding salinity-independent water saturation interpretation (the effect of a mudcake has to be considered, given its thickness and complex permittivity).
3. On-line fluid resistivity (conductivity) measurement in a downhole fluid sampling device such as the Schlumberger MDT tool flowline helps to discriminate filtrate from water-base mud and formation fluids. The conventional MDT resistivity probe saturates at about 24 ohm-m for a hydrocarbon-continuous mixture even if the water fraction is relatively high. This resistivity measurement, when performed during fluid sampling, can potentially fail to detect and sample (water-free) hydrocarbon fluid. By using a microwave probe, the water fraction of both hydrocarbon and water continuous fluids can be estimated from mixture permittivity and/or mixture conductivity measurement, independent of water salinity (estimated under multiphase conditions in the MDT flowline). This provides an improvement in tool efficiency and robustness in discriminating between formation fluids and filtrate from water-base mud (WBM), and the quality of an uncontaminated hydrocarbon sample. Combined with chemical sensing elements for water pH and dominant ion species, a single microwave on-line water conductivity probe provides additional information for the full characterization of formation water. Monitoring of filtrate clean-up for oil-base mud (OBM) when sampling oil is possible, provided there is sufficient complex-permittivity contrast between the OBM and oil.
4. On-line water conductivity measurement of drilling fluids can yield information of changes in the fluid chemistry. There are no sensors capable of monitoring water sampling in wells drilled with WBM. A real-time flowline sensor in the MDT will be desirable to achieve this (where the MDT resistivity cell may have insufficient resolution). By using microwave sensors, water sampling in wells drilled with WBM is better monitored by measuring mixture permittivity, mixture conductivity and water conductivity at the same time, and in real-time.

According to a preferred embodiment of the invention, various hardware components will now be described.

Figure 2A:
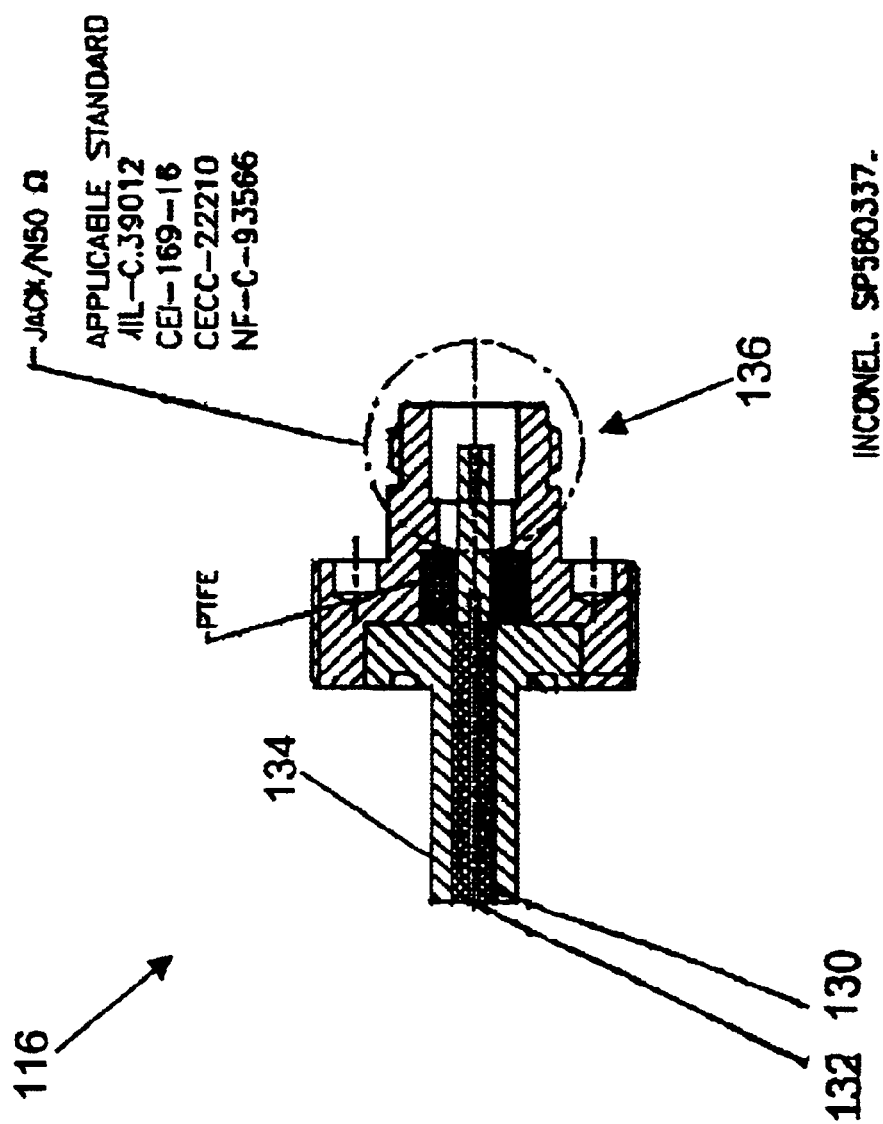
FIGS. 2a and 2b show further detail for an open-coaxial reflection probe, according to a preferred embodiment of the invention.
Figure 2B:
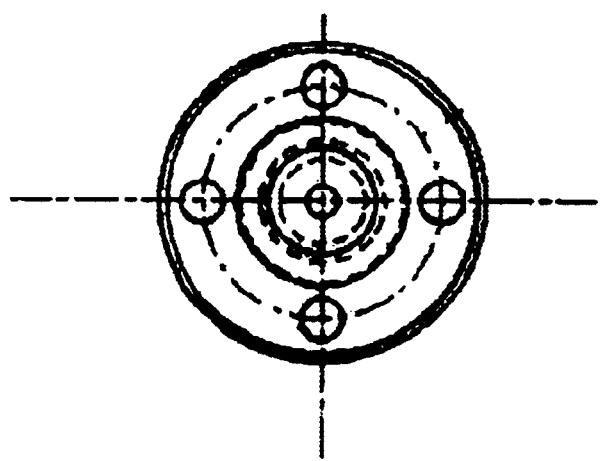

FIG. 1 shows a coaxial probe installed in a pipe wall, according to a preferred embodiment of the invention. A single microwave open-ended coaxial probe 116 is flush mounted at the pipe wall 118, in contact with a (water-oil) liquid layer 114 shown in this example entrained with gas. The inner conductor of the probe 116 has an outer radius a, its outer conductor has an inner radius b; the probe insulator (which is thermally and electrically stable, preferably ceramics or glass) is of dielectric constant $\in_L$. The appropriate choice of a, b and $\in_L$ determines the characteristic impedance $Z_o$ (such as 50Ω) of probe 116. The probe 116 is connected to a microwave reflectometer 110 by a microwave coaxial cable 112 preferably having the characteristic impedance $Z_o$. The microwave reflectometer 110 yields measurement of complex reflection coefficient ρ which is related to complex reflection coefficient Γ at the probe aperture. FIGS. 2a and 2b show further detail for the open-coaxial reflection probe, according to a preferred embodiment of the invention. Borosilicate 7070 (glass) is used as the insulator 130 for probe 116. Tungsten is used for the inner conductor 132. Inconel is used for the outer conductor 134. Connector 136 is of N type. FIG. 2b is another view from the connector side of probe 116.

Figure 3A:
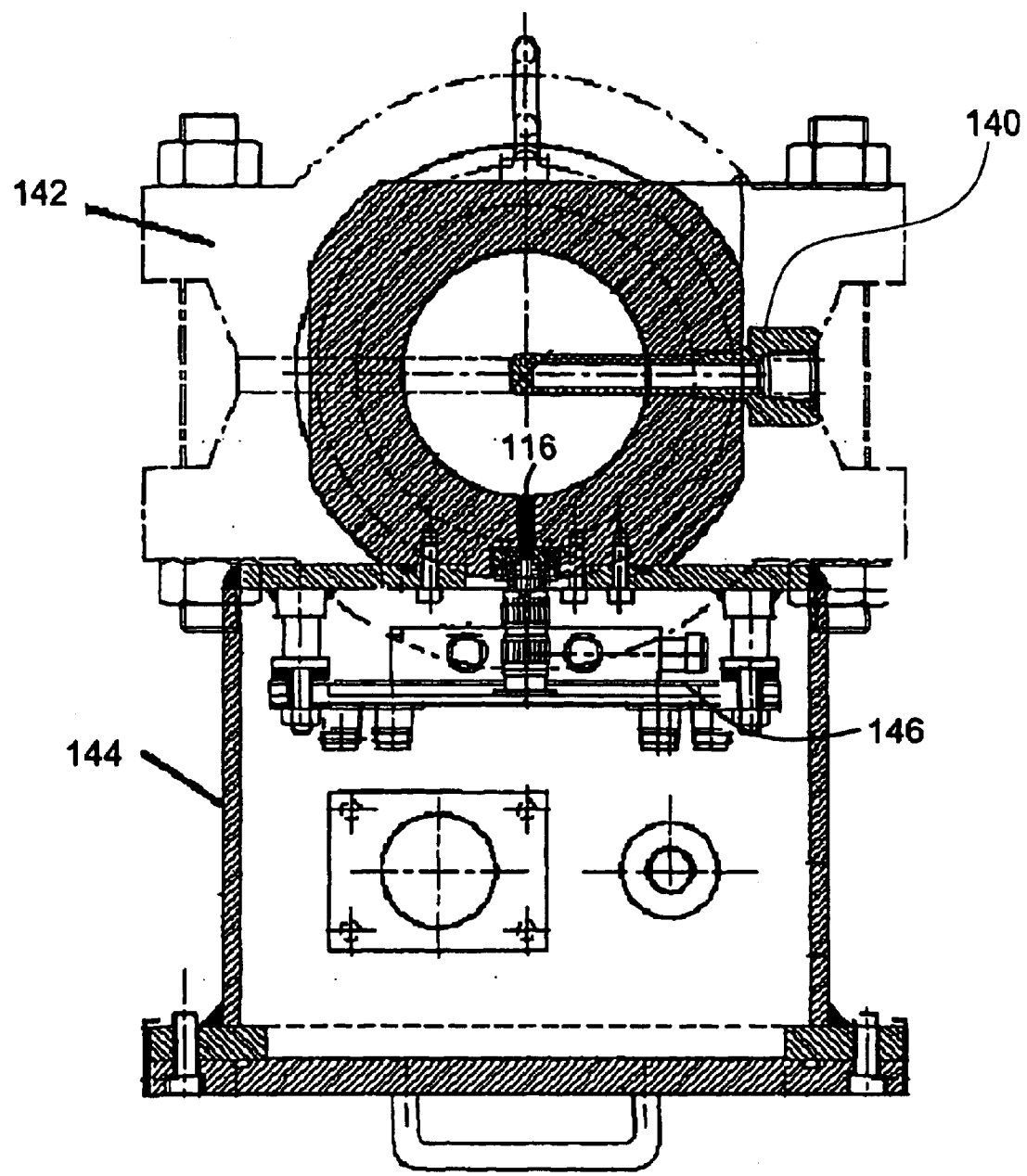
FIG. 3a is a cross sectional drawing of an microwave open coaxial probe assembly mounted in a spool piece, according to a preferred embodiment of the invention.

FIG. 3a is a cross sectional drawing of an microwave open coaxial probe assembly mounted in a spool piece, according to a preferred embodiment of the invention. The coaxial probe 116 is shown mounted at the underside of a measurement spool piece 142 (4" inner diameter (10 cm)) together with a horizontally mounted temperature probe 140. An RF electronics board 146 is mounted beneath the coaxial probe 116 and housed in an explosion proof enclosure 144. The pressure rating of the enclosure is 10,000 psi.

Figure 3B:
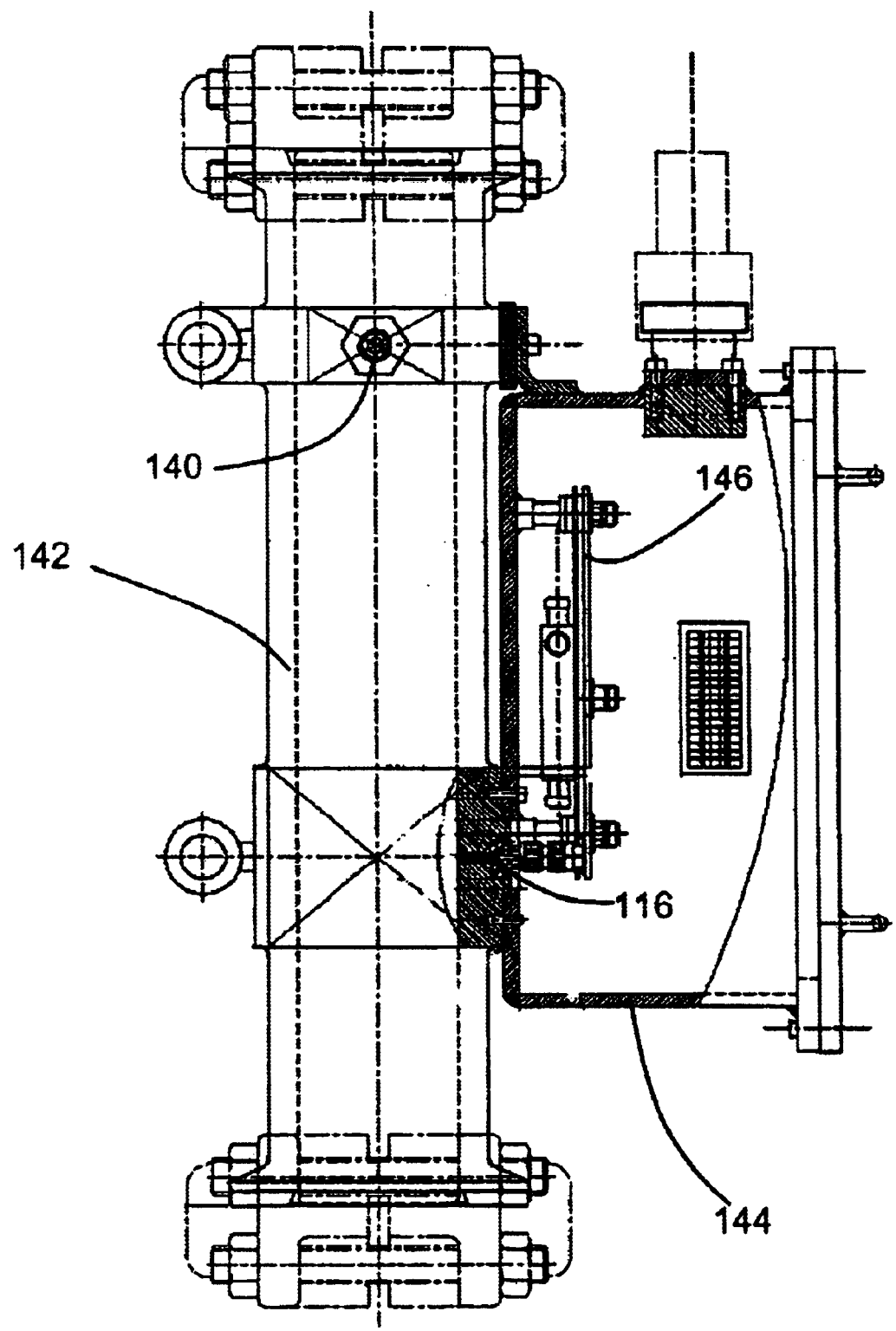

FIG. 3b is longitudinal view of the coaxial probe 116 mounted in the spool piece shown in FIG. 3a.

Figure 4:
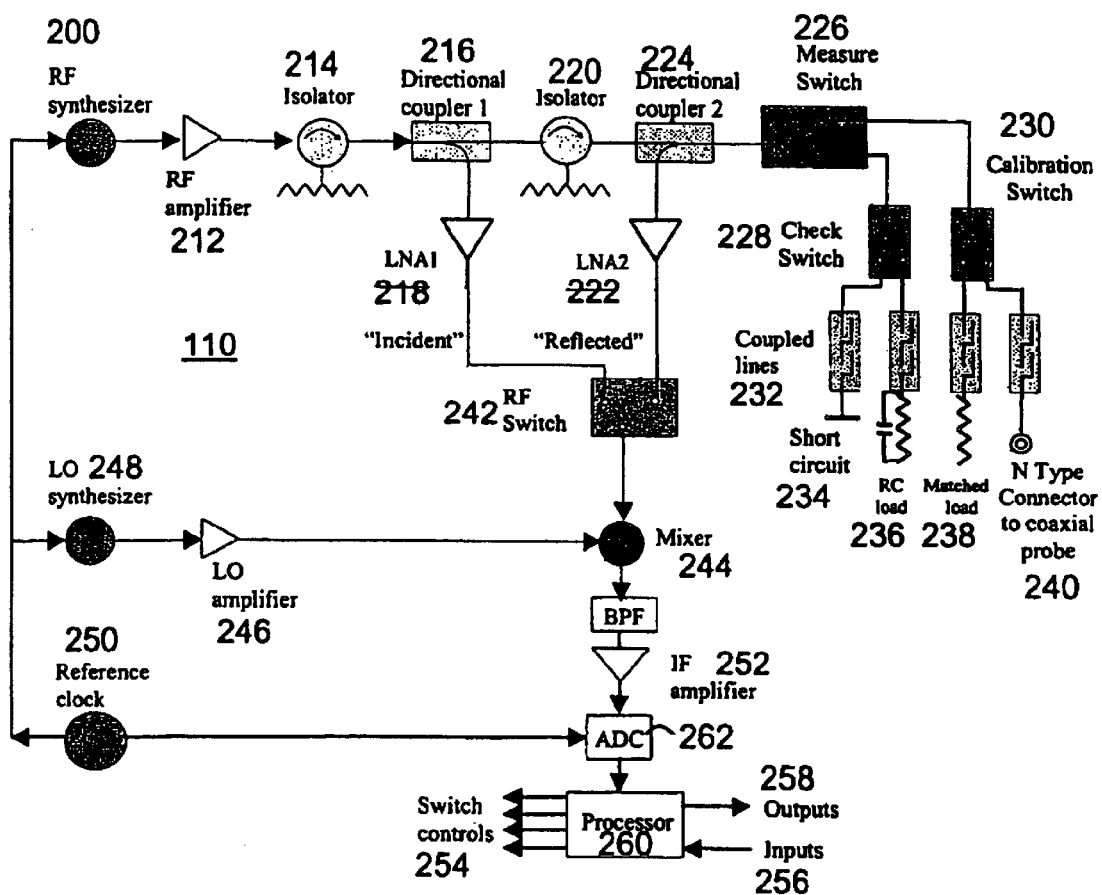
FIG. 4 is a diagram of a microwave frequency reflectometer, according to a preferred embodiment of the invention.

FIG. 4 is a diagram of a microwave frequency reflectometer, according to a preferred embodiment of the invention. Reflectometer 110 is of a single microwave frequency (about 2 GHz, selected to cover high conductivity range expected in production waters, to maintain adequate accuracy in the measured reflection coefficient, and to have low electronics cost). For a desired Intermediate-Frequency (IF, a few tens of kHz), two frequency synthesizers (such as devices based on phase-locked loops connected to a Reference Clock) generate the RF frequency (RF synthesizer 200) and the corresponding LO frequency (LO synthesizer 248). The output of RF synthesizer 200 is amplified by an RF amplifier 212 isolated by an isolator 214; that of LO synthesizer 248 is amplified by an LO amplifier 246. The 'Incident' signal is typically a small fraction of the transmitting RF power sampled by a first unidirectional coupler 216 and amplified by a low noise amplifier (LNA) 218. The 'Reflected' signal is that received by a second unidirectional coupler 224 and amplified by low noise amplifier 222. According to this embodiment, two unidirectional couplers 216 and 224, in back to back arrangement, are used. However, commercial compact components of desired directivity specification could alternatively be used if available. Additionally, a single bi-directional coupler could be used instead if available.

According to a preferred embodiment the overall system directivity is 40 dB (or 0.01 absolute accuracy in the reflection coefficient measurement). The two unidirectional couplers 216 and 224 are each of 30 dB directivity. The additional isolator 220 between them is to increase the directivity of the first coupler 216 (for measuring the incident signal). The directivity of the second coupler 224 (used to measure the reflected signal) can be improved by using a periodic calibration procedure (as described below). An RF switch 242 selects alternately the 'Incident' and the 'Reflected' signals for down-conversion to the respective IF signals by a mixer 244, which are then band-pass filtered (BPF) and amplified by an IF amplifier 252. The 'Incident' and the 'Reflected' IF (sinusoidal) voltage waveforms are digitized by an analog to digital converter (ADC) 262. For example, ADC 262 takes 4 samples per IF period with sampling rate of 4*IF. Their amplitude and phase are reconstructed by a Processor 260, which also controls the sequencing RF switch 242 and calibration/check switches 228 and 230. The absolute amplitude-attenuation and phase-shift (M,θ) of the RF reflection signal is then calculated from amplitude ratio and phase difference of the 'Reflected' with respect to the 'Incident'.

To achieve good system stability and improved directivity over a wide range of operating temperatures, the RF electronics is designed with built-in calibration standards (short circuit 234, matched load 238 and RC check load 236) for performing periodic electronics calibration (by calibration switch 230) and check (by check switch 228). Specific design of coupled lines 232 in series with the RF cables are for hazardous area safety purposes, such as in hazardous area Zone 0. N-type connector 240 is connected to probe connector 136 of probe 116 (shown in FIG. 2a). Additionally, all of the components shown in FIG. 4 are preferably located within the enclosure 144 and on circuit board 146. According to another embodiment, the processor 260 and related hardware is located on a separate PC computer.

Further detail will now be provided regarding mixture conductivity vs. mixture permittivity parameter space. The measured incident and reflected complex signals that are recorded by processor 260 in FIG. 4 can be used to derive the complex reflection coefficient at the probe aperture $\Gamma=(Z_c-Z_o)/(Z_c+Z_o)$, which is a measure of the mismatch between the probe characteristic impedance $Z_o$ and its aperture impedance $Z_c=[j\omega C(\in^*)]^{-1}$ ($\omega=2\pi f$ is the angular frequency)

As an example, referring to FIG. 1, the fringe capacitance of probe 116 can be described as a linear model $C(\in^*)=C_f+\in^* C_o$, $\in^*=\in'-j\in''$ is the relative complex permittivity of the liquid-layer 114 seen by probe 116; $C_f$ and $C_o$ are capacitance parameters characterizing the probe inner and outer fringe capacitances.

Given the true complex reflection coefficient $\Gamma$(=reflected-signal/incident-signal, at the probe aperture) (the microwave reflectometer 110 measures a different complex reflection coefficient ρ, FIG. 1), the probe capacitance can be derived as $$C(\varepsilon^*) = \frac{1-\Gamma}{1+\Gamma}\frac{1}{j\omega Z_o}, \quad (1)$$

and $$\varepsilon^* = \frac{C(\varepsilon^*)-C_f}{C_o} = \left(\frac{1}{j\omega Z_o C_o}\right)\left(\frac{1-\Gamma}{1+\Gamma}\right) - \frac{C_f}{C_o}. \quad (2)$$

See e.g. Marsland T P and Evans S: "Dielectric measurements with an open-ended coaxial probe", IEE Proceedings Pt.H, Vol.134, No.4, August 1997, 341–349. The following calibration model has been proposed relating desired complex permittivity $\in_m^*$ to the measured reflection coefficient $\rho_m$, by using three calibration fluids with known complex permittivities($\in_1,\in_2,\in_3$); viz.

$$\varepsilon_m^* = -\left[\frac{\Delta_{m1}\Delta_{32}\varepsilon_3\varepsilon_2 + \Delta_{m2}\Delta_{13}\varepsilon_1\varepsilon_3 + \Delta_{m3}\Delta_{21}\varepsilon_2\varepsilon_1}{\Delta_{m1}\Delta_{32}\varepsilon_1 + \Delta_{m2}\Delta_{13}\varepsilon_2 + \Delta_{m3}\Delta_{21}\varepsilon_3}\right] \quad (3)$$

Here $\Delta_{ij}=\rho_i-\rho_j$, the measured reflection coefficients ($\rho_1, \rho_2, \rho_3$) correspond to the three calibration fluids. Equation 3 shows that complex permittivity $\in^*$ can be derived as a function of the measured reflection coefficient $\rho_m$, without the need of the knowledge of the probe model capacitances $C_o$ and $C_f$ (of equation 2). This calibration procedure takes care of electrical-length between the probe and its connector, and all spurious effects (internal reflections, inaccurate mechanical dimensions, etc.). The selection of three-calibration fluids is preferably air/water/saline.

The derived complex permittivity $\in^*=\in'-j\in''$ is related to the effective conductivity and dielectric properties of the mixture near the probe through $\in^*=\in_m-j\sigma_m/(\omega\in_o)$; here $\in_m$ and $\sigma_m$ are the apparent mixture (relative) permittivity and conductivity; $\in_o\approx 8.854$ pF/m is the (absolute) permittivity of free space.

Figure 5:
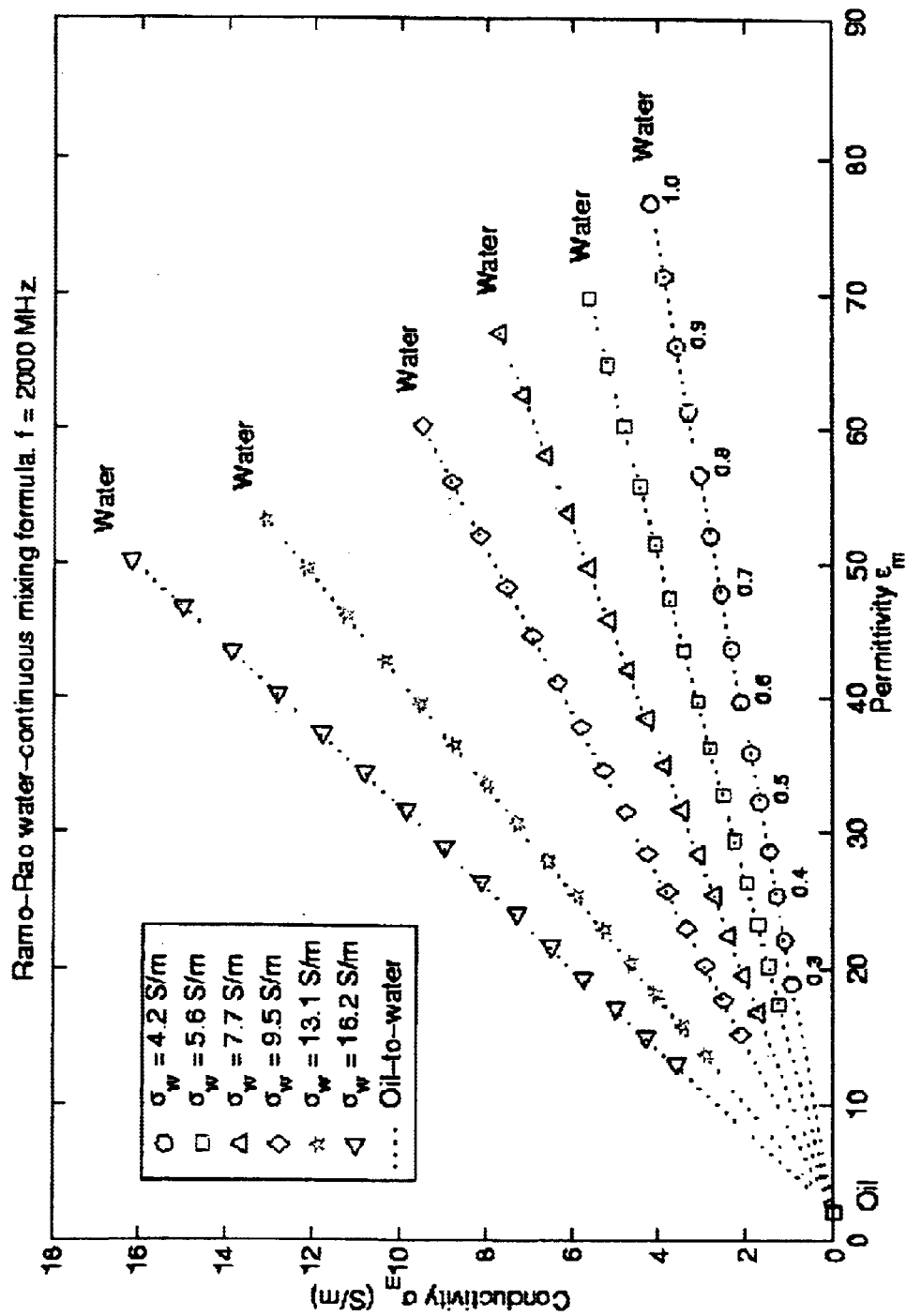
FIG. 5 is a cross-plot of mixture conductivity $\sigma_m$ vs. mixture permittivity $\in_m$ of water-continuous water/oil mixtures.

FIG. 5 is a cross-plot of $\sigma_m$ vs. $\in_m$ of water-continuous water/oil mixtures. FIG. 5 shows six water conductivities ($\sigma_w$=4.2 to 16.2 S/m.) and water-cut (WLR) from 1.0 to 0.3 with 0.05 step, labeled for mixtures with $\sigma_w$=4.2 S/m. Oil permittivity is 2.1, and oil conductivity is $10^{-8}$ S/m. The cross-plot is calculated from formulae derived by Ramu and Rao for liquid/liquid mixture permittivity and conductivity ($\in_m,\sigma_m$) (See Hammer E A: "Flow permittivity models and their applications in multiphase meters", Proc. Multiphase Metering, IBC Technical Services, 12–13 March 1997, Aberdeen; Hammer E A: "Three component flow measurement in oil/gas/water mixtures using capacitance transducers", Ph.D. Thesis, UMIST, U.K., 1983.) The Ramu and Rao formulae are as follows.

$$\varepsilon_m = \frac{\varepsilon_1(\theta\gamma + k^2\xi\delta) + \sigma_1(\xi\gamma - \theta\delta)}{\gamma^2 + k^2\delta^2} \quad \text{(A1a)}$$

$$\sigma_m = \frac{\sigma_1(\theta\gamma + k^2\xi\delta) + \varepsilon_1 k^2(\xi\gamma - \theta\delta)}{\gamma^2 + k^2\delta^2} \quad \text{(A1b)}$$

where $k=\omega\in_o$, $\omega=2\pi f$, $\in_o=8.854$ pF/m; $\sigma_1,\sigma_2=$ conductivity of the continuous and the dispersed phase, respectively; $\in_1,\in_2=$ relative permittivity of the continuous and the dispersed phase, respectively; and $\theta=(2\sigma_1+\sigma_2)+2v(\sigma_2-\sigma_1)$ $\delta=(2\in_1+\in_2)-v(\in_2-\in_1)$ $\xi=(2\in_1+\in_2)+2v(\in_2-\in_1)$ $\gamma=(2\sigma_1+\sigma_2)-v(\sigma_2-\sigma_1)$ where v is the volume fraction of the dispersed phase. The counterpart mixing formulae of Bruggeman's are:

$$\frac{\varepsilon_2 - \varepsilon_m}{\varepsilon_2 - \varepsilon_1}\left(\frac{\varepsilon_1}{\varepsilon_m}\right)^{1/3} = 1 - v \quad \text{(A2a)}$$

$$\frac{\sigma_2 - \sigma_m}{\sigma_2 - \sigma_1}\left(\frac{\sigma_1}{\sigma_m}\right)^{1/3} = 1 - v \quad \text{(A2b)}$$

See, Hammer E A: "Three component flow measurement in oil/gas/water mixtures using capacitance transducers", Ph.D. Thesis, UMIST, U.K., 1983.

The water permittivity are selected the same as the experimental data shown in FIG. 6 (described below) for easy cross-comparison. For each fixed water conductivity, as WLR varies, $(\sigma_m, \in_m)$ data points are of the same slope, falling close on the oil-to-water line. Note that the slopes in the $\in_m$-$\sigma_m$ parameter space are simply $S_m=\sigma_m/(\in_m-\in_{oil})$ and $S_w=\sigma_w/(\in_w-\in_{oil})$. For water-continuous flows, there are generally $\sigma_w>>\sigma_{oil}$ and $\sigma_m>>\sigma_{oil}$. From Bruggeman's mixing laws (see equations A2a and A2b), it can be readily derived, by demanding equal volume fractions v, that $\sigma_m/\in_m=(S_m/S_w)^3\sigma_w/\in_w$. With the slopes of the mixture and single-phase water being equal (i.e. $S_m/S_w=1$), for water-continuous flows we have $\sigma_m/\in_m\approx\sigma_w/\in_w$.

Figure 6:
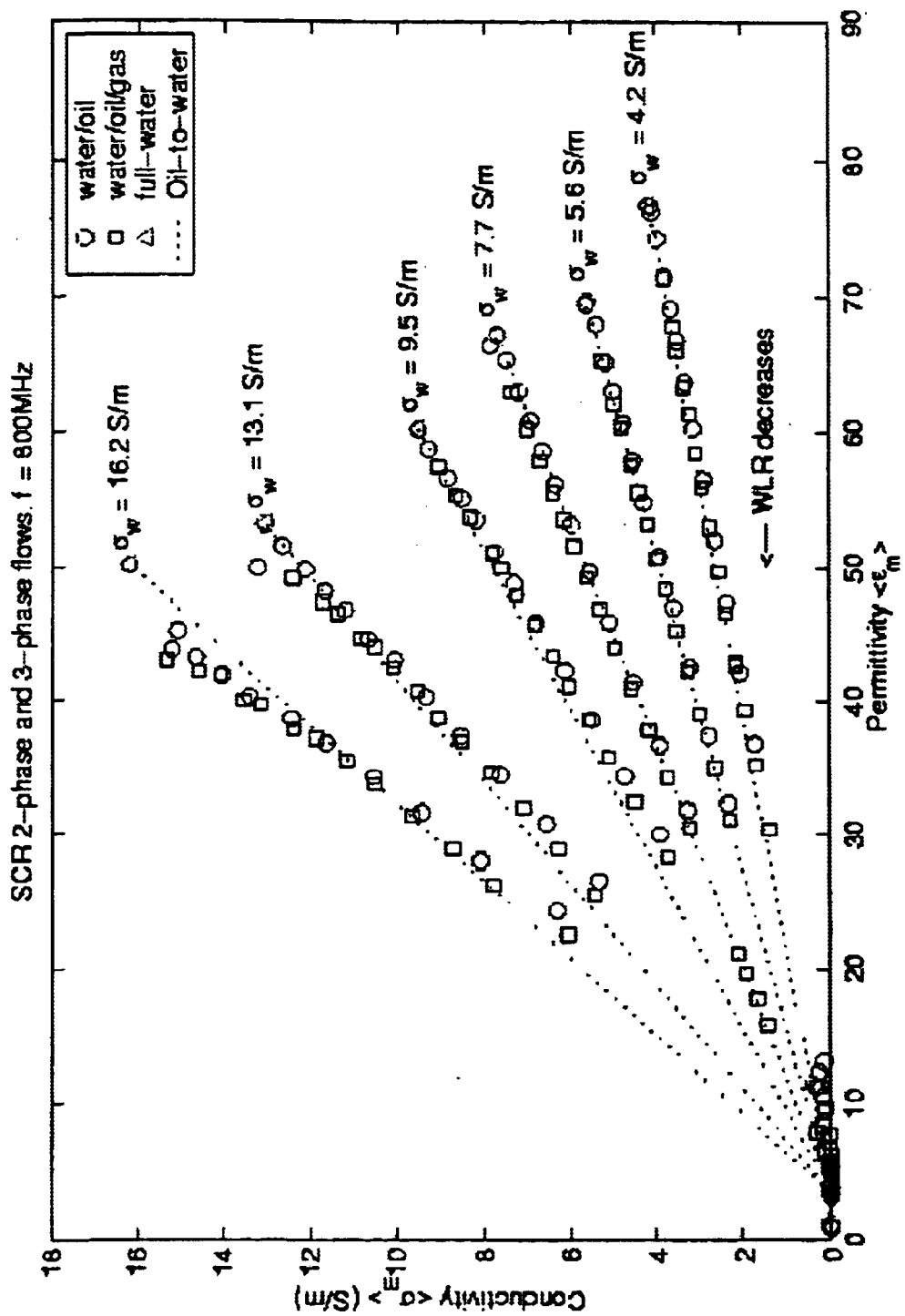
FIG. 6 is a cross-plot of $\sigma_m$ vs. $\in_m$ measured by an open coaxial probe flush mounted at pipe wall.

FIG. 6 is a cross-plot of $\sigma_m$ vs. $\in_m$ measured by an open coaxial probe flush mounted at pipe wall. The data are plotted for both water/oil flows and water/oil/gas flows over a wide range of water conductivity (from 4.2 to 16.2 S/m). The probe was operating at 800 MHz, and oil-continuous flows of low $\sigma_m$ (WLR<0.35). Both $\sigma_m$ vs. $\in_m$ are the time-averages (over 60 seconds) of their instantaneous values. The cross plot indicates that, even with gas present, when water is continuous, the data points in the mixture conductivity and mixture permittivity parameter space fall close to the oil-to-water line for each fixed water conductivity. This is because, when water is rich, the complex reflection coefficient is dominated by the presence of water (large term in the complex permittivity), whereas the gas and oil (hydrocarbon) have small and similar complex permittivities. It is also because hydrocarbon (gas and oil) volume fraction influences $\sigma_m$ and $\in_m$ in the similar way when water is continuous.

Figure 7:
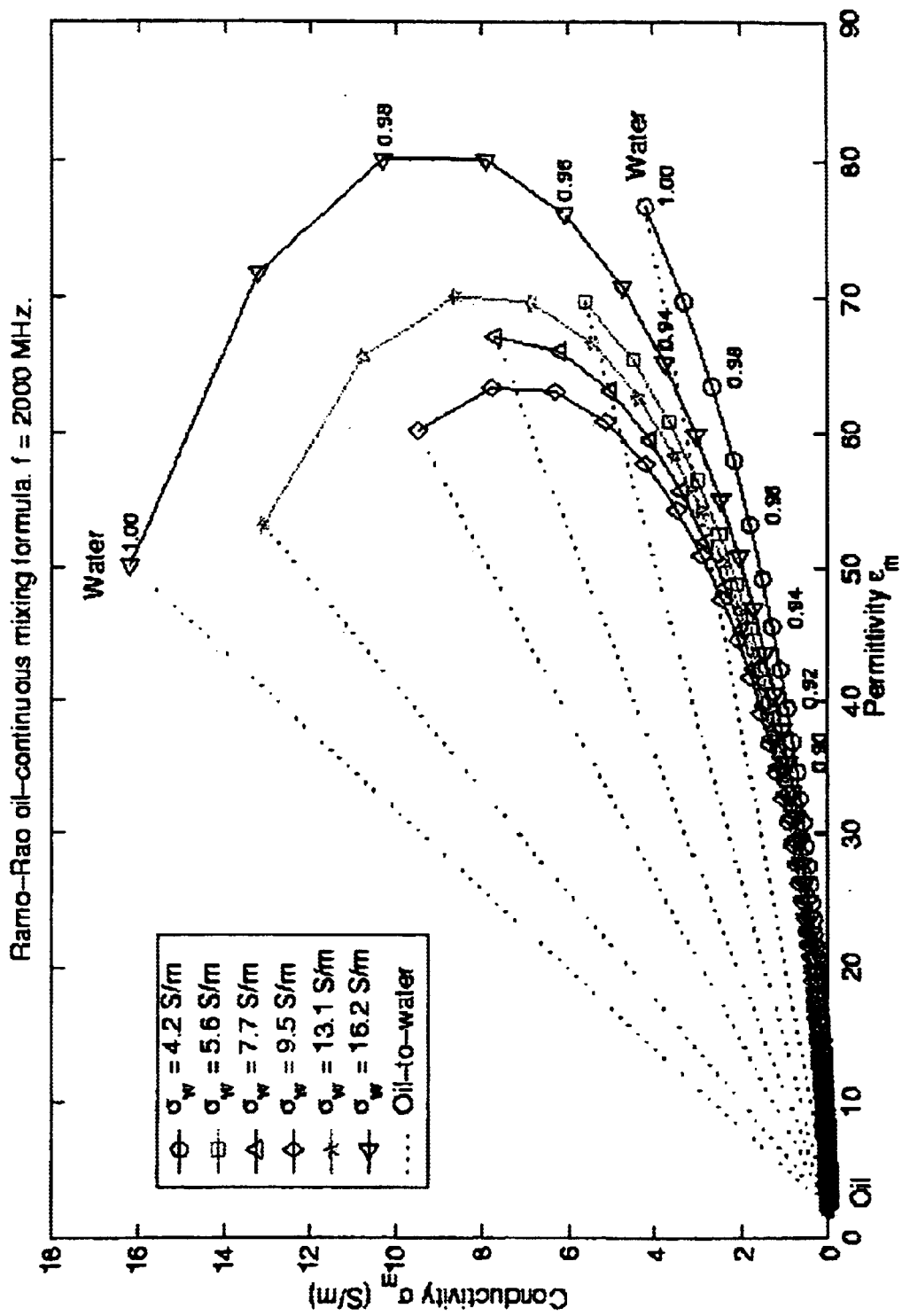
FIG. 7 is a cross-plot $\sigma_m$ vs. $\in_m$ of oil-continuous water/oil mixtures.

FIG. 7 is a cross-plot $\sigma_m$ vs. $\in_m$ of oil-continuous water/oil mixtures. The plot in FIG. 7 uses the oil-continuous mixing formulae of Ramu-Rao (at 2000 MHz). FIG. 7 shows six water conductivities $\sigma_w=4.2$ to 16.2 S/m. Water-cut (WLR) is from 1.0 to 0.0 with 0.01 step, partially labeled for mixtures with $\sigma_w=4.2$ S/m. Note that when WLR is low, the $\sigma_m$ vs. $\in_m$ cross-plot reveals little sensitivity to water conductivity. However, as WLR of oil-rich flows becomes sufficiently high (for high viscosity oil), the dependence of $\sigma_m$ vs. $\in_m$ cross-plot on water conductivity becomes evident, with distinct curve formed for each fixed water conductivity. This is observed experimentally and an illustration is given in FIG. 8 (described below) when the flow rates of oil and gas (of small gas bubbles) are relatively high (i.e. the open-coaxial probe immersed in water are mainly oil/gas wet). Increasing the size of gas bubbles (at reduced gas rate) has led to the probe being wetted intermittently by water-rich and oil/gas-rich mixtures (See FIG. 9a discussed below).

Figure 8:
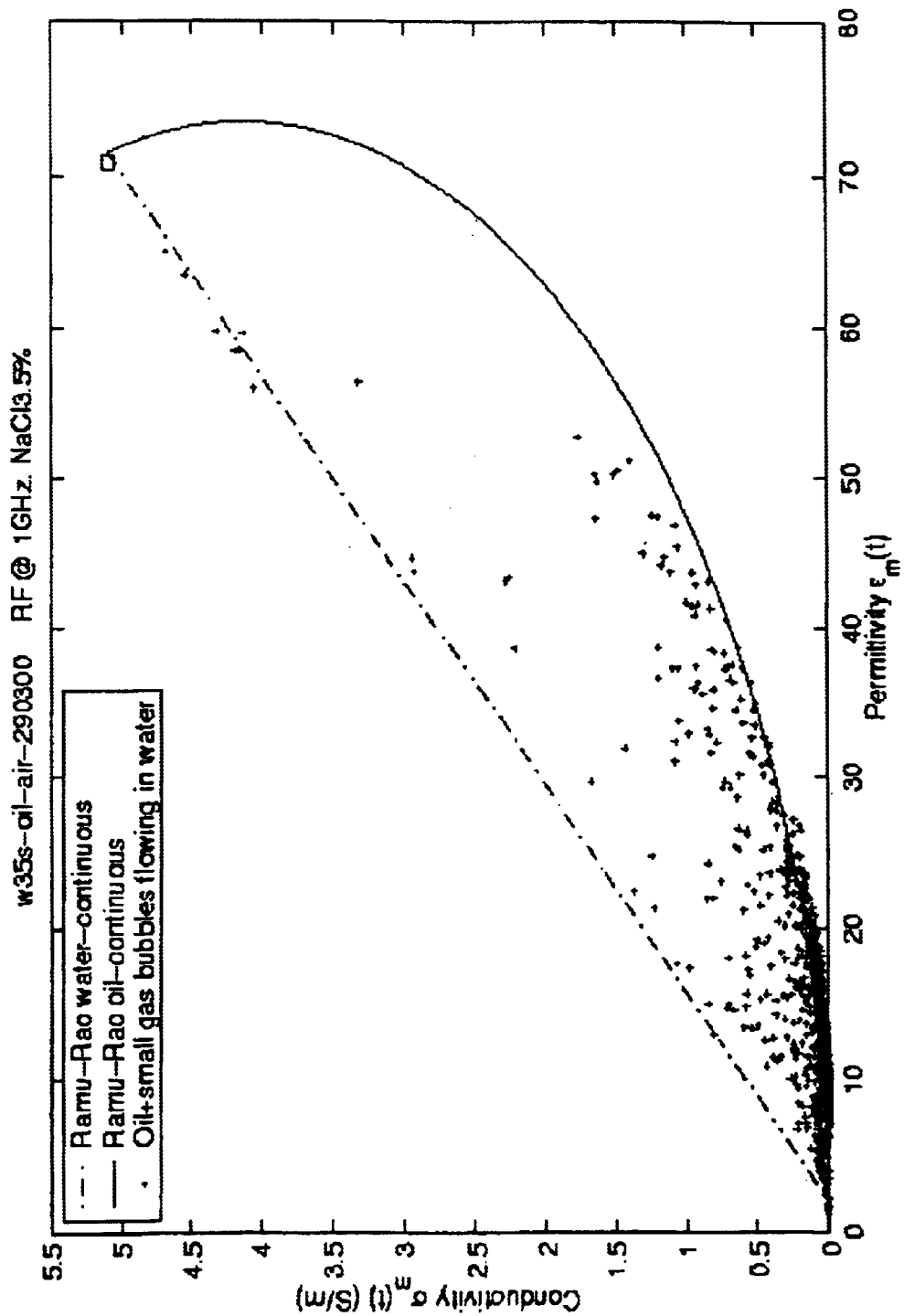
FIG. 8 is a cross-plot of open-coaxial probe measured $\sigma_m(t)$ vs. $\in_m(t)$ for smaller gas bubbles.

FIG. 8 is a cross-plot of open-coaxial probe measured $\sigma_m(t)$ vs. $\in_m(t)$ (10 Hz data). The test results of oil/gas (small gas bubbles) mixtures flowing in water of $\sigma_w=5.1$ S/m (relatively high oil and gas flow rates). The probe (immersed in water tank) was largely oil/gas wet; the majority of data points lies close to the Ramu-Rao predicted oil-continuous curve. The probe was operating at 1 GHz.

Figure 9A:
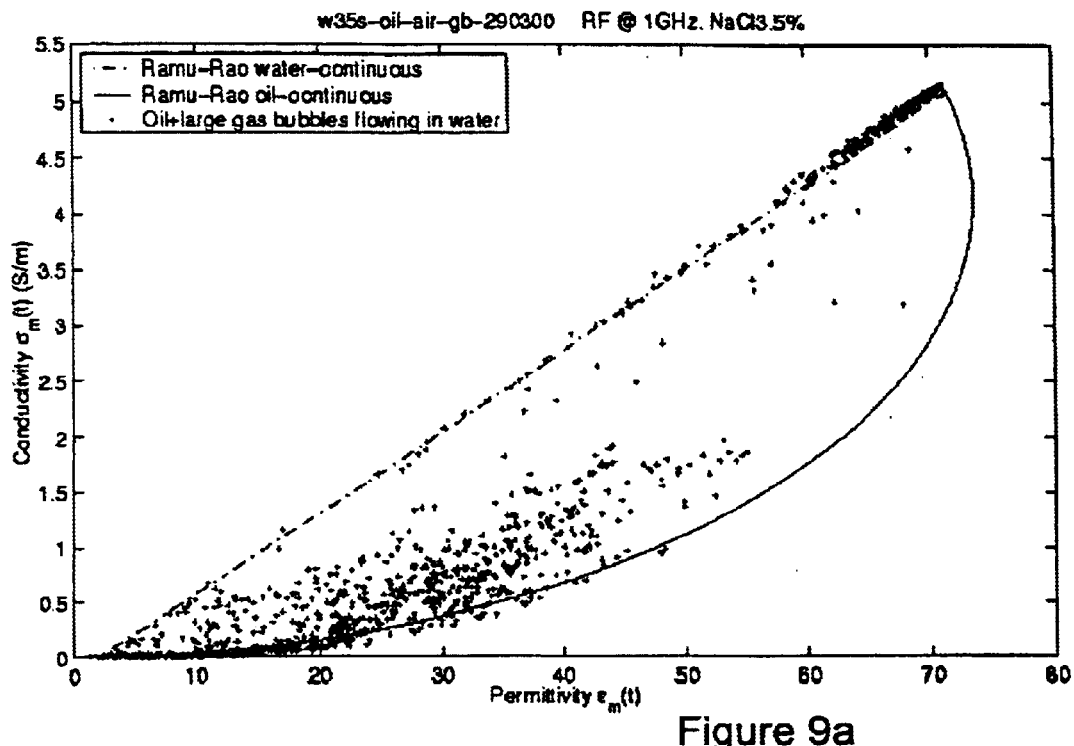
FIG. 9a is a cross-plot of open-coaxial probe measured $\sigma_m(t)$ vs. $\in_m(t)$ for larger gas bubbles.
Figure 9B:
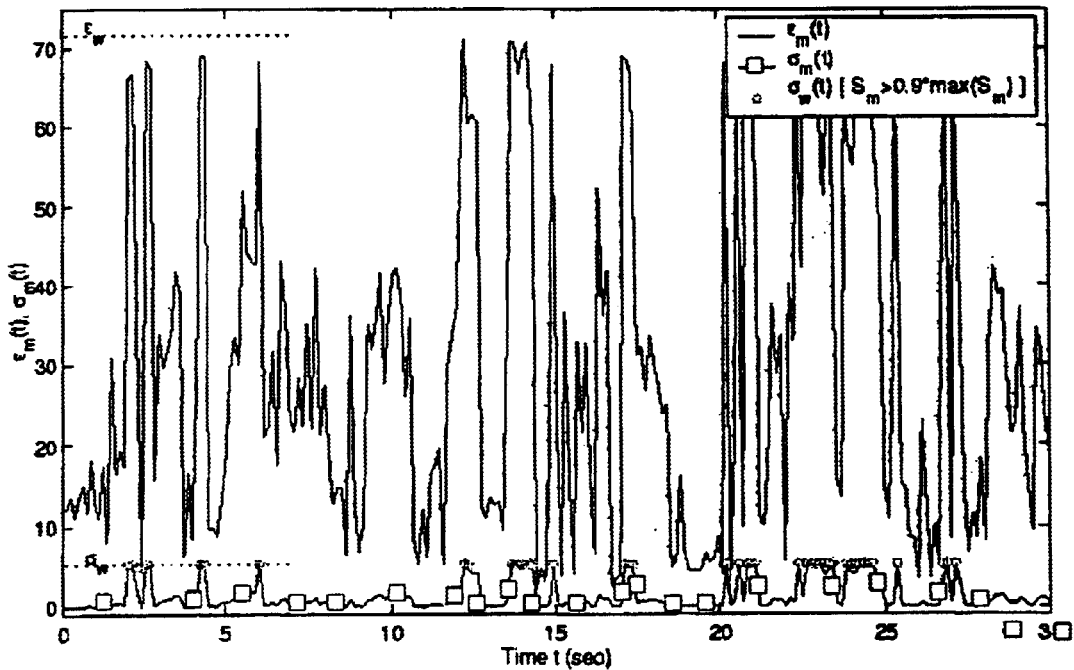

FIG. 9a is a cross-plot of open-coaxial probe measured $\sigma_m(t)$ vs. $\in_m(t)$. FIG. 9a is similar to FIG. 8 but for test results of oil/gas (large gas bubbles) mixtures flowing in water (of $\sigma_w=5.1$ S/m, reduced gas flow rate). The probe (immersed in water) was intermittently water and oil/gas wet. FIG. 9b is a time series of the 10-Hz $\sigma_m(t)$ and $\in_m(t)$ data corresponding to FIG. 9a. An instantaneous water conductivity estimate $\sigma_m(t)$ also shown for the water-rich part of the signals, with the selected slope as $S_m(t)=\sigma_m(t)/[\in_m(t)-\in_{oil}]>0.9* \max[S_m(t)]$.

On-line water conductivity interpretation according to a preferred embodiment of the invention will now be discussed. An important benefit of working in the $(\in_m, \sigma_m)$ parameter space is to utilize the fundamental relationship between their end (single-phase water) points. The brine permittivity and conductivity, $\in_w$ and $\sigma_w$, as a function of temperature T and salinity s, can be empirically correlated as below:

$$\in_w(s,T)=\in_w(0,T)-K_{\in_o}(s,T)\sigma_w(s,T) \quad (4)$$

where $\in_w(0,T)$ is the well-established temperature correlation of pure water permittivity (s=0); $K_{\in_o}(s,T)$ is an empirical factor which decreases with increasing temperature and is largely salinity independent. This feature of $K_{\in_o}(s,T)$ is indicated in FIG. 10b (discussed below), and derived from the Stogyrn correlations for NaCl solution (low-frequency) water permittivity $\in_w(s,T)$ and conductivity $\sigma_w(s,T)$ (see FIG. 10a). See Stogryn A, "Equations for calculating the dielectric constant of saline water", *IEEE Transactions on Microwave Theory and Techniques*, August 1971, pp.733–36. The mean values $<K_{\in_o}(T)>$ for T=0 to 50° C., are also shown in FIG. 10b (discussed below).

The NaCl salt solution static dielectric constant and conductivity as function of salinity and temperature are reproduced below from A. Stogyrn, 1971.

The complex dielectric constant of saline:

$$\varepsilon^* = \varepsilon_\infty + \frac{\varepsilon_s - \varepsilon_\infty}{1+j\omega\tau} - j\frac{\sigma}{\omega\varepsilon_o}$$

with high-frequency dielectric constant $\in_\infty\approx5$ (has little dependence on temperature and on salinity).

NaCl solution normality N is related to its salinity s (in parts/thousand or kppm) below (for $0\leq s\leq 260$):

$$N=s(1.707\times10^{-2}+1.205\times10^{-5}s+4.058\times10^{-9}s^2)$$

The dependence of static dielectric constant ($\in_s$) and dielectric relaxation time ($\tau$ in ps) on temperature T (°C.) and normality N is reproduced below (for $0 \leq T \leq 40°$ C. and $0 \leq N \leq 3$):

$$\in_s(T,N) = \in_s(T,0)a(N)$$

$$2\pi\tau(T,N) = 2\pi\tau(T,0)b(N,T)$$

$$\in_s(T,0) = 87.74 - 4.0008 \times 10^{-1}T + 9.398 \times 10^{-4}T^2 - 1.410 \times 10^{-6}T^3$$

(for the pure-water static permittivity $\in_s(T,0)$ above with $0 \leq T \leq 100$, see, Malmberg C G and Maryott A A, "Dielectric constant of water from 0° to 100° C.", *Journal of Research National Bureau of Standards*, Vol.56, No.1, January 1956, RP2641,).

$$2\pi\tau(T,0) = 1.1109 \times 10^2 - 3.824T + 6.938 \times 10^{-2}T^2 - 5.096 \times 10^{-4}T^3$$

$$a(N) = 1.000 - 0.2551N + 5.151 \times 10^{-2}N^2 - 6.889 \times 10^{-3}N^3$$

$$b(N,T) = 0.1463 \times 10^{-2}NT + 1.000 - 0.04896N - 0.02967N^2 + 5.644 \times 10^{-3}N^3$$

NaCl solution conductivity ($\sigma$ in S/m) dependence on temperature T (° C., $\Delta = 25.0 - T$) and normality N is follows:

$$\sigma(T, N) = \sigma(25, N) \times$$
$$\left\{ \begin{array}{l} 1.000 - 1.962 \times 10^{-2}\Delta + 8.08 \times 10^{-5}\Delta^2 - \\ \Delta N[3.020 \times 10^{-5} + 3.922 \times 10^{-5}\Delta + N(1.721 \times 10^{-5} - 6.584 \times 10^{-6}\Delta)] \end{array} \right\}$$

$$\sigma(25, N) = N(10.394 - 2.3776N + 0.68258N^2 - 0.13538N^3 + 1.0086 \times 10^{-2}N^4)$$

Figure 10A:
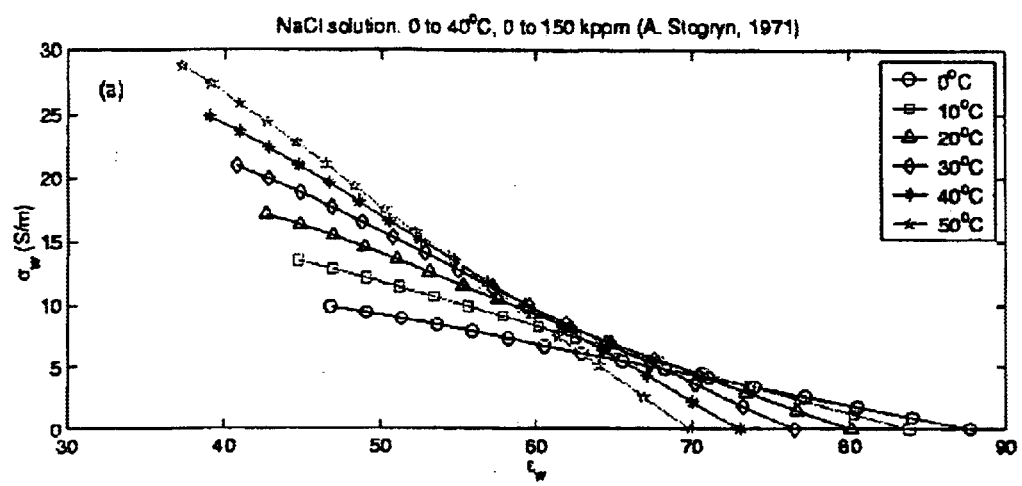
FIGS. 10a and 10b are plots water conductivity vs. water permittivity and the factor K vs. salinity respectively.
Figure 10B:
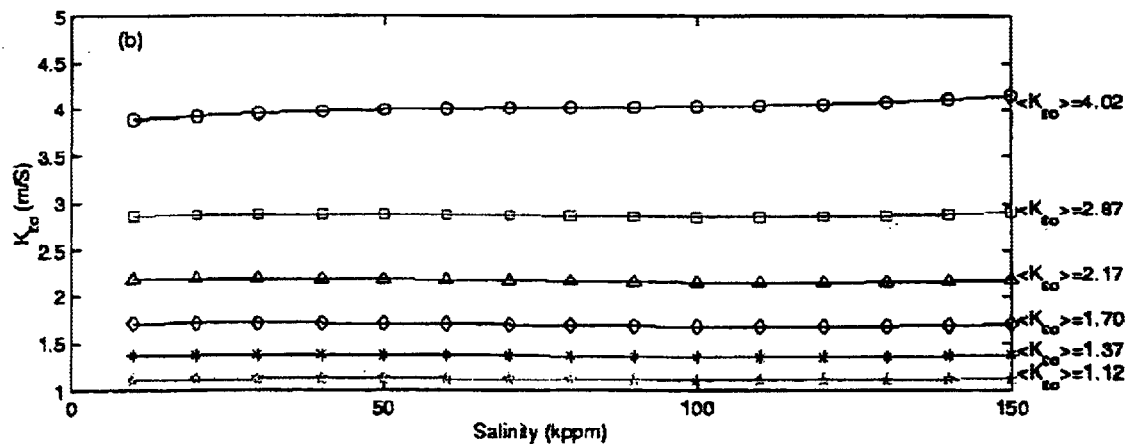

FIGS. 10a and 10b are plots based on correlations from Stogyrn. The following applies to FIG. 10a. The end points of the ($\in_m, \sigma_m$) space are (low-frequency) water conductivity $\sigma_w(s,T)$ vs. the permittivity $\in_w(s,T)$, plotted for NaCl saline water over T=0 to 50° C., salinity s=0 to 150 kppm at 10 kppm increment. For each temperature, s=0 point at the rightmost, s=150 kppm on the leftmost. In FIG. 10b, the factor $K_{\in o}(s,T)$ in equation 4 is plotted vs. salinity s of NaCl salt solution with T=0 to 50° C., and mean value $<K_{\in o}(T)>$ over the salinity range is also shown.

To obtain a water conductivity estimate $\hat{\sigma}_w$ for water continuous flows, the simplest embodiment (although others are possible) is to utilize equation (4) and demand that the slopes in the $\in_m - \sigma_m$ space under multiphase and single-phase water conditions are equal. That is by requiring $S_m = \sigma_m/(\in_m - \in_b) = S_w = \sigma_w/(\in_w - \in_b)$, the following relationship is derived (largely, the values of intercept permittivity $\in_b = \in_{oil}$):

$$\hat{\sigma}_w = [\in_w(0,T) - \in_b]S_m/(1 + <K_{\in o}(T)> S_m) \quad (5)$$

Figure 11:
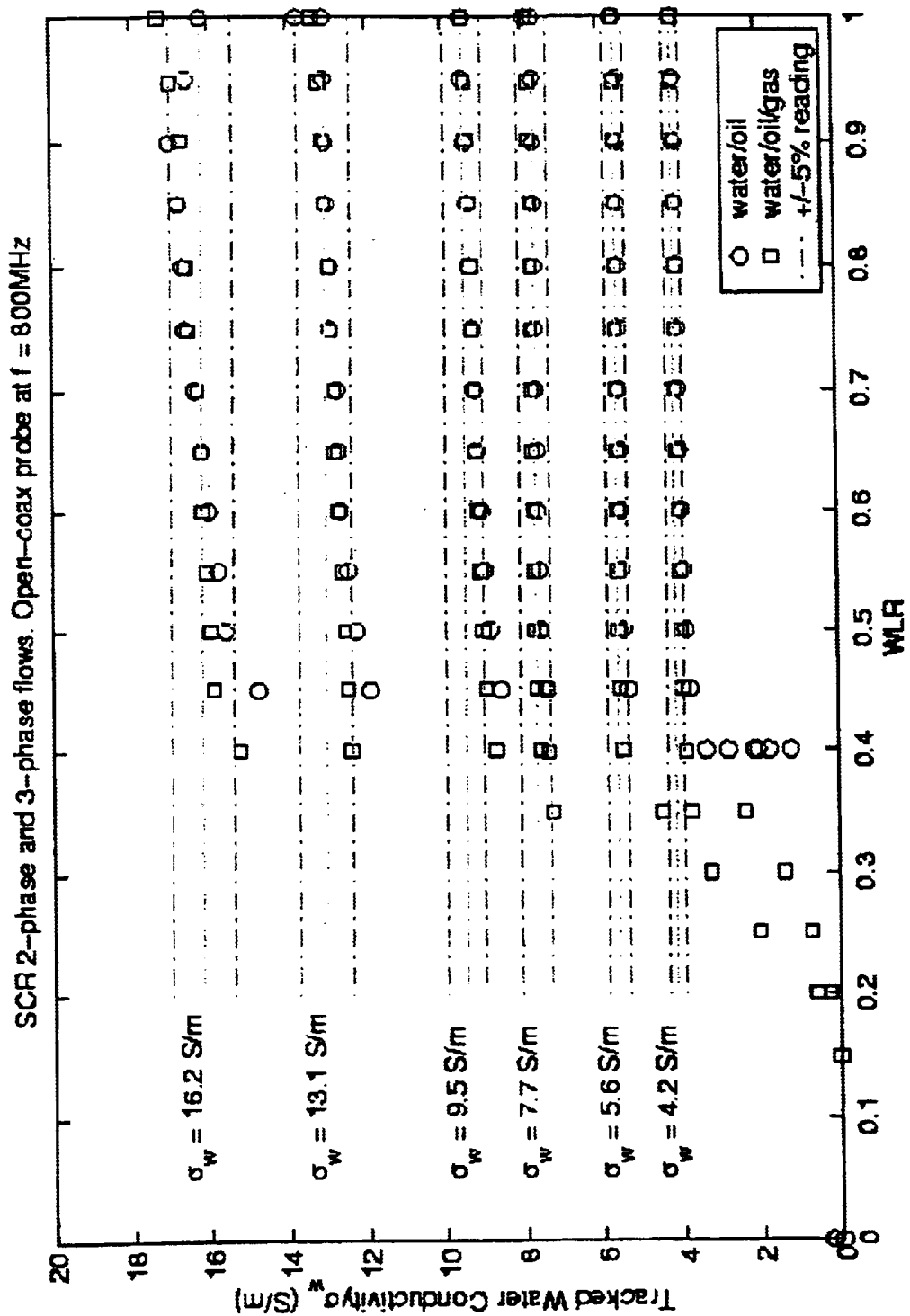
FIG. 11 shows tracked water conductivity vs. water-cut (WLR)

FIG. 11 shows tracked water conductivity vs. water-cut (WLR). The on-line estimate of water conductivity $\hat{\sigma}_w$ is from equation (5). $<K_{\in o}(T)>$ is equal to 1.85, and the slope $S_m = \sigma_m/(\in_m - \in_b)$ data is from FIG. 6. The water/oil and water/oil/gas flows are with $\sigma_w = 4.2$ to 16.2 S/m. FIG. 11 shows that, by fixing $<K_{\in o}(T)> = 1.85$ (at about 16° C.), the on-line water conductivity estimate for the three-phase dataset in FIG. 6 are mostly made correct within ±5% of reading, for water-continuous flows (water-cut>0.4). For intermittently oil/water continuous flow mixtures, it is possible to select water-rich segments of the time-series signals $\in_m(t)$ and $\sigma_m(t)$ to achieve instantaneous water conductivity estimate; this is illustrated in FIG. 9b.

For oil-continuous flow mixtures, a more sophisticated interpretation scheme is preferably used to estimate water conductivity.

For NaCl, $CaCl_2$, KCl and $MgSO_4$ pure-salt solutions at about 20° C., the conductivity and permittivity both have been found to be dependent on the salt species and the salinity. However, at salinities below 100 kppm, the distinction between NaCl and other pure salt solutions is small. In view of the fact that most formation waters are dominated by the NaCl salt species, the relatively small proportion of the other salts (tested with 50/50 wt % mixed-salt solutions of $CaCl_2$+NaCl and KCl+NaCl) will make their presence difficult to determine from the bulk conductivity-permittivity measurements. In a mixed salt solution, when NaCl is dominant, the conductivity can be estimated to mostly within ±5% of reading, based on the bulk conductivity-permittivity measurements and on the permittivity-conductivity relation established for pure NaCl solutions. Thus, the simple interpretation model (equation (5)) for on-line water conductivity estimate can be used for most practical applications.

Figure 12:
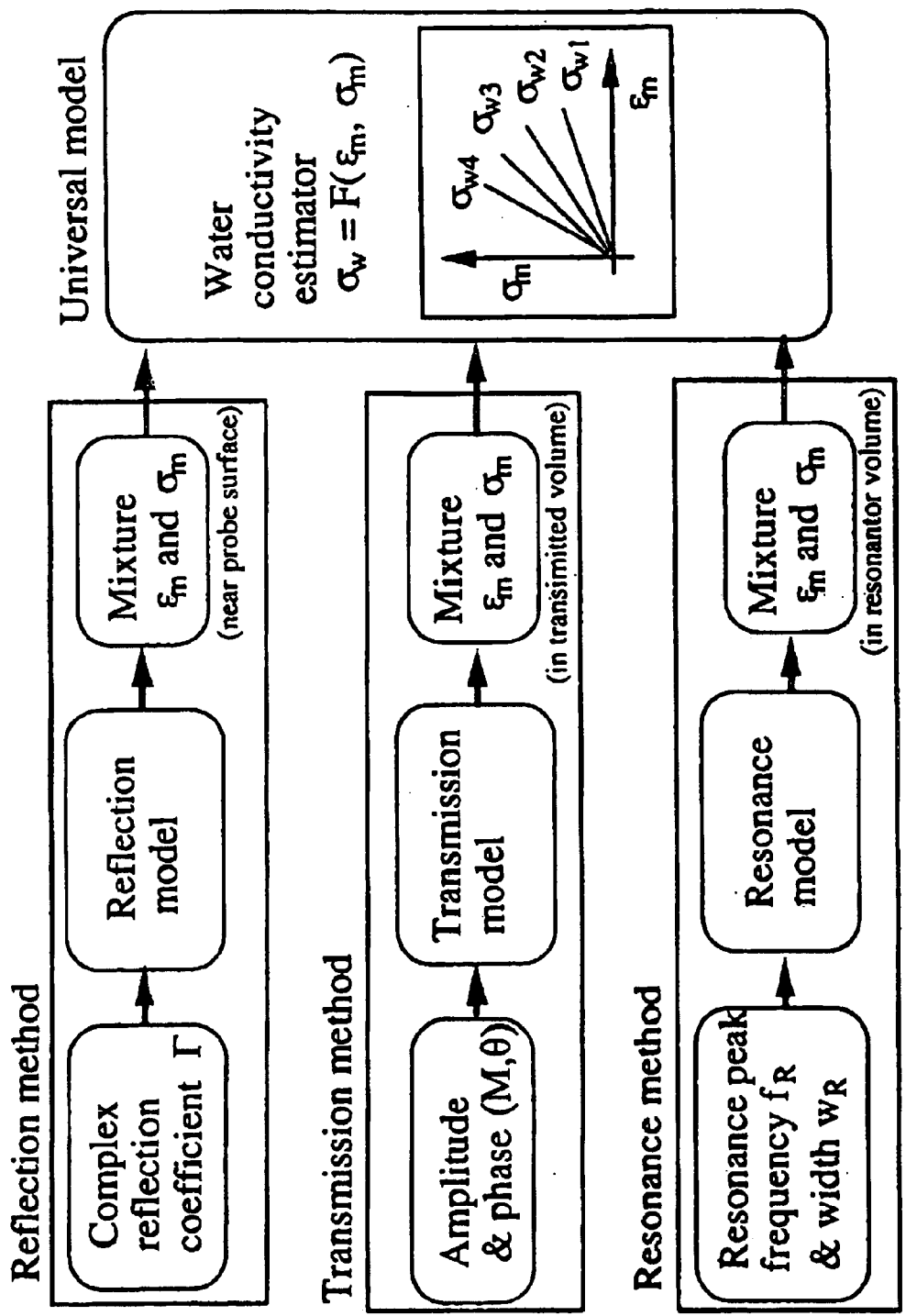
FIG. 12 is a flow chart illustrating methods of estimating water conductivity for reflection, transmission and resonance methods, according to preferred embodiments of the invention.

The present invention is also applicable to other microwave techniques. FIG. 12 is a flow chart illustrating methods of estimating water conductivity for reflection, transmission and resonance methods, according to preferred embodiments of the invention. Each method makes use of a related sensing physics model to transform the raw measurements (reflection coefficient, amplitude-attenuation and phase-shift, resonance peak frequency and its width) into mixture permittivity and conductivity ($\in_m, \sigma_m$). The model of estimating water conductivity $\sigma_w$ from ($\in_m, \sigma_m$) is applicable to all methods. In a transmission method, at least a pair of transmission and receiving antennas are used, mounted at the pipe peripheral (e.g. diametrically) to interrogate the pipe cross-section. By utilizing the amplitude-attenuation and phase-shift measurements (M,θ) (See FIG. 13a, described below) in an appropriate microwave transmission model, the mixture permittivity and conductivity ($\in_m, \sigma_m$) in the transmitting path can derived (See FIG. 13b, described below). The process of estimating water conductivity $\sigma_w$ from the fundamental parameters ($\in_m, \sigma_m$) is similar to that of the reflection method described above.

Figure 13A:
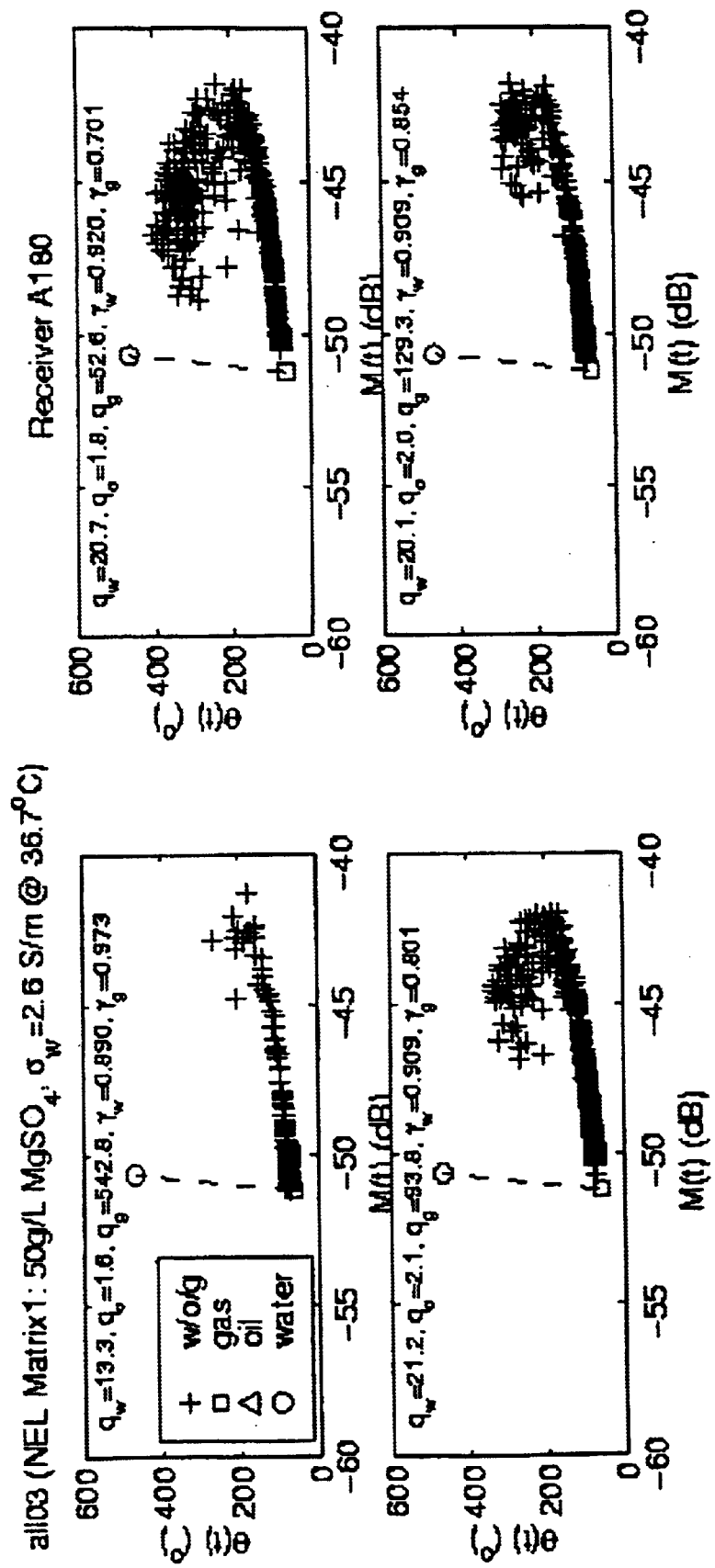
FIGS. 13a and 13b show respectively cross plots of microwave transmission magnitude-attenuation/phase (M,θ) and of derived mixture permitivity conductivity($\in_m,\sigma_m$), for water-continuous 3-phase flows.
Figure 13B:
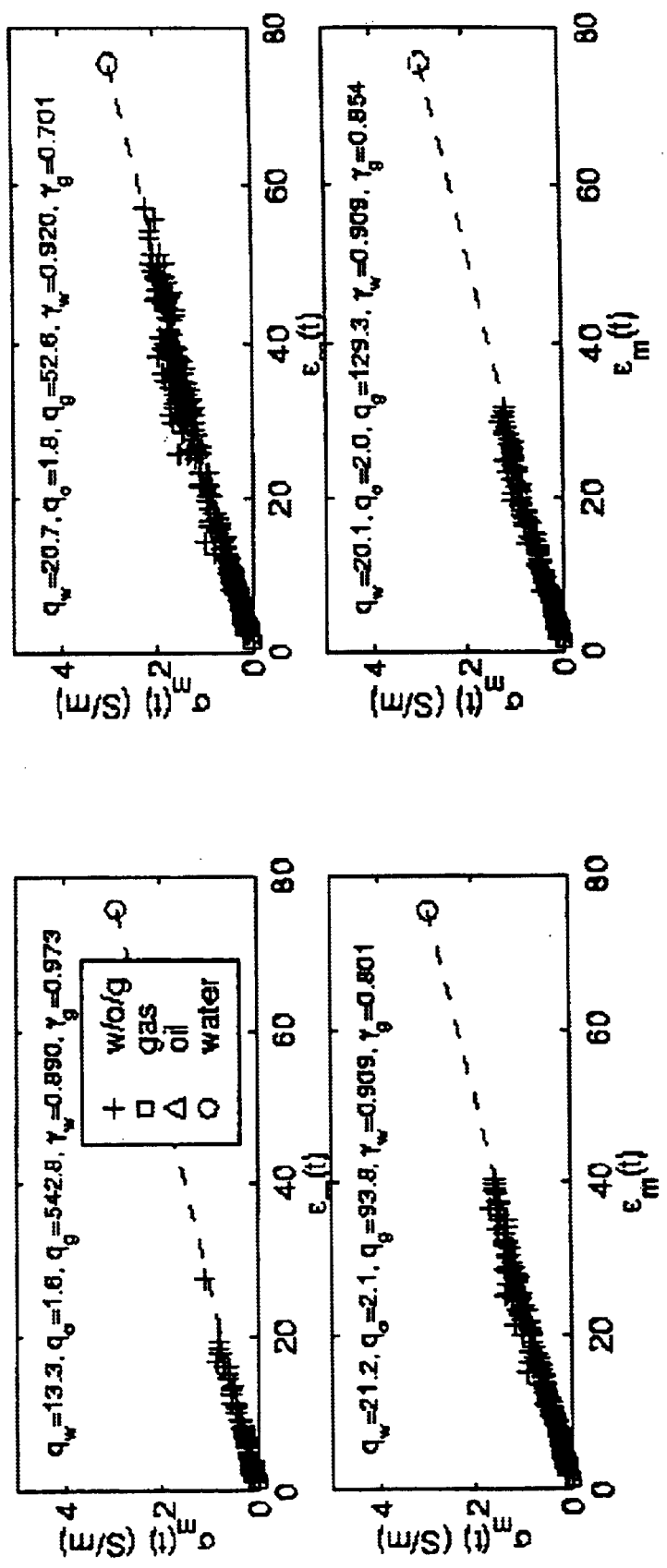

FIGS. 13a and 13b show cross plots for water-continuous 3-phase flows. FIG. 13a shows cross-plots of instantaneous microwave transmission amplitude and phase (M,θ) at 800 MHz. FIG. 13b shows cross plots for the corresponding transformed instantaneous $\in_m$ and $\sigma_m$. Saline is 50 g/l $MgSO_4$, $\sigma_w$, is 2.6 S/m at 37° C., and Forties crude. Flowrates ($q_w, q_o, q_g$) are in units of m³/h. Fractional water-cut $\gamma_w$ and gas-cut $\gamma_g$ are indicated. Single-phase gas, oil and water data measured is also shown. Data with 50 Hz sampling rate is plotted for 10 s duration. Note that the full-water point of such a low conductivity $\sigma_w$ (2.6 S/m) is less attenuative than the gas point.

By examining FIGS. 13a and 13b, the reason for performing water conductivity estimate in the ($\in_m, \sigma_m$) parameter space becomes very clear: the raw amplitude and phase space (M,θ) can be inherently nonlinear and error prone (e.g. when performing time averaging). The non-linearity in the instantaneous (M,θ) space is illustrated in FIG. 13a for a 3-phase water-continuous flow. In time, the amplitude M swings well beyond the range bounded by the single-phase (gas, oil and water) data, mainly due to the presence of gas slugs (about 90% water-cut and gas-cuts from 70% to 97%). As shown in FIG. 13b, in the new transformed instantaneous mixture permittivity and conductivity ($\in_m(t), \sigma_m(t)$) space, three-phase flow data points are bounded, close to the oil-to-water line. This greatly linearized ($\in_m, \sigma_m$) parameter space is also inherently more suitable for water-cut estimate (e.g. from equation A2).

For a microwave resonance method, an exciting antenna and a receiving antenna can be mounted around a suitable pipe structure (cavity, open-ended or short-ended coaxial transmission-line or others). By exciting the resonator over a range of microwave frequencies, the peak frequency and its width ($f_R$, $w_R$) of resonance mode(s) of interest can be measured. In a microwave resonance model, the peak frequency is generally related to the bulk mixture permittivity in the resonator ($\in_m = (f_o/f_R)^2$, $f_o$ is the empty-pipe resonant frequency); whereas the peak width is indicative of loss therein and thus related to bulk mixture conductivity ($\sigma_m$ directly related to $w_R$). In a similar way, water conductivity $\sigma_w$ can then be estimated from the measured ($\in_m, \sigma_m$) parameter space.

As a byproduct of on-line water conductivity estimation $\hat{\sigma}_w$ (and also $\hat{\in}_w$ from equation (4)), salinity independent water-cut estimate of the liquid-layer near the probe is possible, by inputting the measured mixture conductivity $\sigma_m$ (or $\in_m$) in a conductivity (or permittivity) mixing-law.

Figure 14:
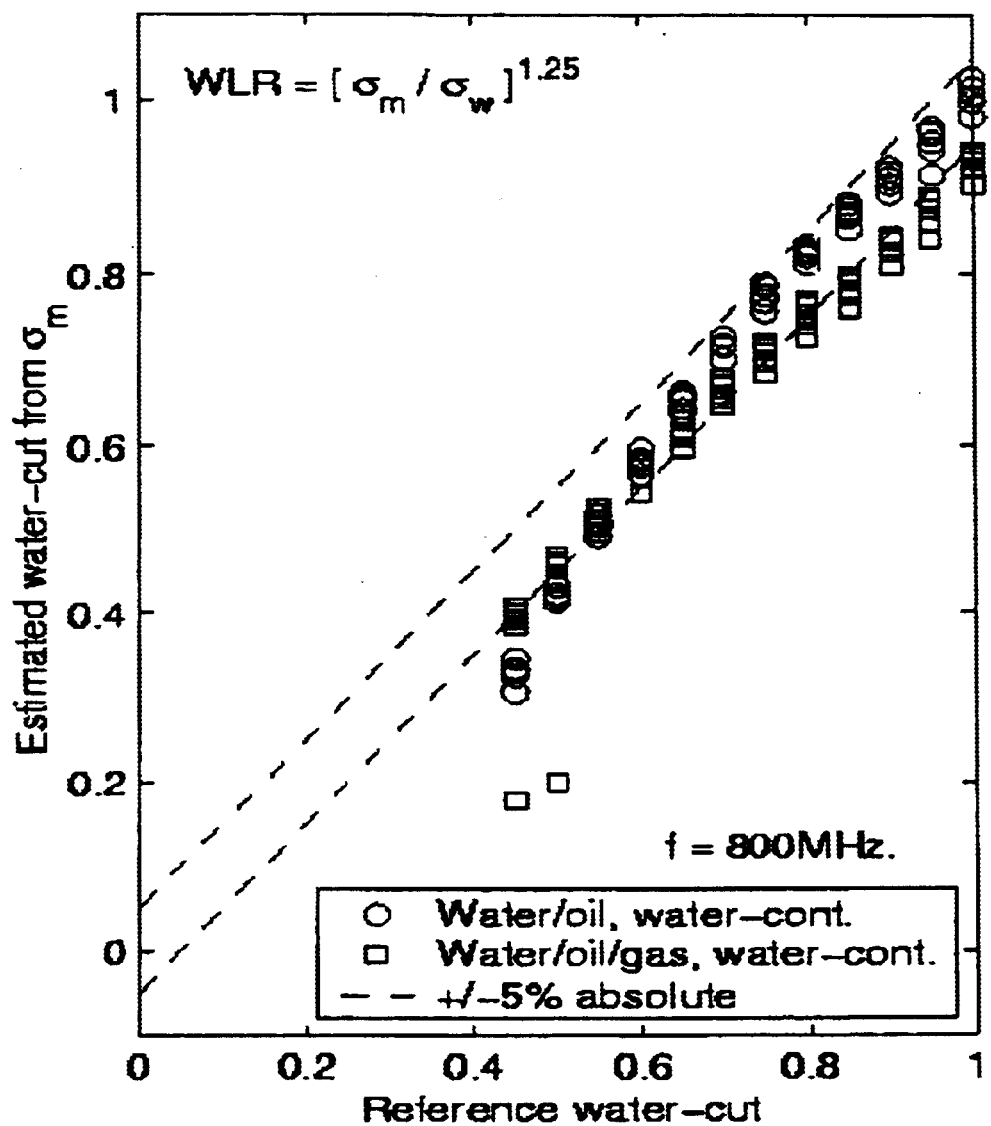
FIG. 14 is a plot showing estimated water cut for water-continuous oil/water and oil/water/gas (gas-cut 45% to 65%) flows shown in FIG. 6.

FIG. 14 is a plot showing estimated water cut for water-continuous oil/water and oil/water/gas (gas-cut 45% to 65%) flows shown in FIG. 6. Water-cut is estimated from mixture conductivity $\sigma_m$ measured by the open-coaxial probe at 800 MHz, with WLR=$(\sigma_m/\sigma_w)^{1.25}$. Six water conductivities from 4.2 to 16.2 S/m are shown. A similar water-cut estimate can be obtained from $\in_m$ based on $[(\in_m - \in_{oil})/(\in_w - \in_{oil})]^{1.25}$.

The modification of a uniform mixing law is often useful because within the probe's shallow depth of investigation, the oil/water mixture is often not uniform. As shown in FIG. 14, water-cut tends to be underestimated when there is significant gas entrainment, based on time-averaged mixture conductivity and permittivity. By fast sampling, it is possible to remove segments of signals with high gas entrainment, leaving the liquid-rich segment for time-averaging for deriving water-cut with a reduced bias.

By using microwave reflection (and/or transmission) method, the continuous liquid (water or oil) phase can be readily detected from the measured mixture permittivity and conductivity ($\in_m, \sigma_m$) (for oil-continuous flows, both are at low values). The on-line detection of the continuous liquid phase and the measured water-cut (and hence fraction $\alpha$) will help in accurately determining liquid viscosity $\mu_{liquid}$, based on, e.g. the Einstein law $\mu_{liquid} = \mu_{continuous} (1 + 0.5\alpha_{dispersed})/(1 - \alpha_{dispersed})$, for the gas-liquid slip and venturi discharge coefficient calculation.

Different microwave methods can be combined. Water conductivity estimate from a microwave reflection probe capable of covering a wider range of conductivity, water cut and gas cut, can be used as an input to a microwave system based on transmission or resonance method. The combined microwave system can provide more robust water holdup and thus water cut measurements, largely independent of water salinity.

Figure 15:
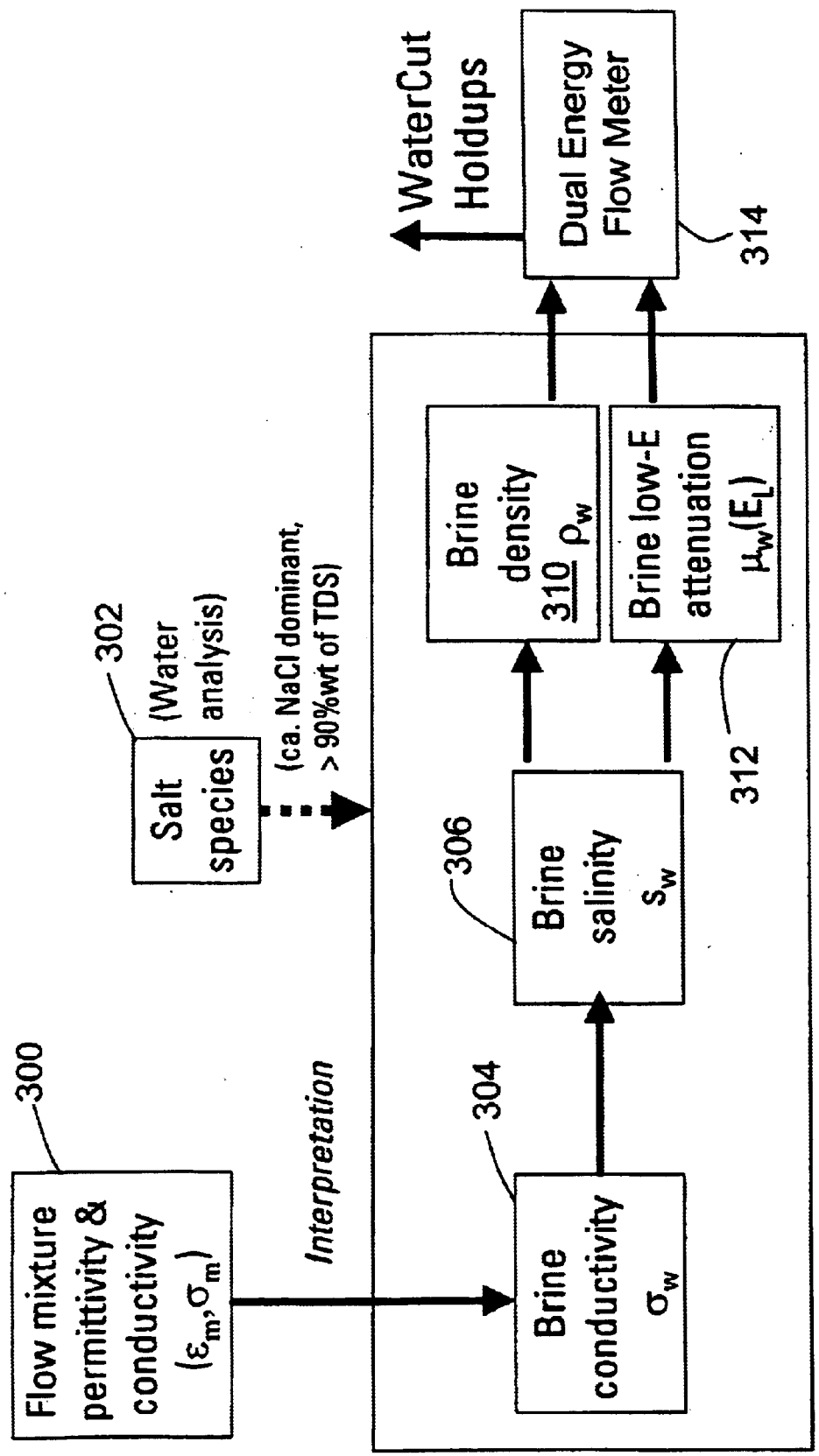
FIG. 15 is a flow chart showing the use of the on-line water conductivity estimate for salinity correction of a dual energy flow meter, according to a preferred embodiment of the invention.

FIG. 15 is a flow chart showing the use of the on-line water conductivity estimate for salinity correction of a dual energy flow meter, according to a preferred embodiment of the invention. The on-line water conductivity estimation can be used to achieve correction to the brine low-energy mass attenuation of a multiphase meter such as PhaseTester™ and PhaseWatcher™ type flow meters from 3-Phase Measurement A. S. The flow mixture permittivity and conductivity ($\in_m, \sigma_m$) 300 is used to estimate water conductivity 304 according to the invention as described above. The translation of water salinity ($S_w$) 306 from water conductivity ($\sigma_w$) 304 is done given the knowledge of the dominant salt species 302 and temperature (for example from probe 140 shown in FIGS. 3a and 3b). Salt species 302 is typically dominated by NaCl (e.g. larger than 90% by weight of total dissolved solids (TDS)).

Given the mass attenuations of pure water ($\mu_{H2O}$) and pure salt species ($\mu_{NaCl}$) 302, the saline water mass attenuation 312 can be easily calculated from the salt composition and salinity 306. For example, the mass attenuation of NaCl water solution of salinity $S_{w(NaCl)}$ is computed from below:

$$\mu_w = (1 - S_{w(NaCl)})\mu_{H2O} + S_{w(NaCl)}\mu_{NaCl} \quad (6)$$

and that for a saline containing NaCl and $CaCl_2$ of salinities $S_{w(NaCl)}$ and $S_{w(CaCl2)}$ is:

$$\mu_w = (1 - S_{w(NaCl)} - S_{w(CaCl2)})\mu_{H2O} + S_{w(NaCl)}\mu_{NaCl} + S_{w(CaCl2)}\mu_{CaCl2} \quad (7)$$

In order to determine water density 310 based on the salinity 306 the following relationship can be used. The (NaCl) brine density at atmospheric pressure is a function of salinity and temperature. According to A. M. Rowe and J. C. S. Chou (*Journal of Chemical and Engineering Data*, Vol 15, No. 1, 1970):

$$\frac{1}{\rho_w} = A(T) + sD(T) + s^2 E(T) - P\left[B(T) + PC(T) + s\left(F(T) + sG(T) + \frac{1}{2}PH(T)\right)\right] \quad (8)$$

where s=the salinity in g of NaCl per g of solution; 0 to 0.25 g/g (250 kppm); T=the absolute temperature in Kelvin, from 273 to 448 K (0 to 175° C.); P=the absolute pressure in kg/cm2 (0.980665 bar), from 1 to 350 kg/cm2; $\rho_w$=the density in g/cm³ (or g/cc). The coeffients A-H as a function of Temperature are defined according to A. M. Rowe and J. C. S. Chou (*Journal of Chemical and Engineering Data*, Vol 15, No. 1, 1970.

From relatively fresh-water to NaCl salt saturated water, the brine low-energy mass attenuation of flow meter 314 can be corrected to about ±2% by using brine salinity estimate based on its conductivity measured within ±5%. This typically translates into correcting a water-cut measurement error to about ±6%. Without the brine conductivity information, the relative error in the brine low-energy mass attenuation can be up to 50%. The on-line water density estimate 310 is preferably used to improve the accuracy of the water cut and gas-water-oil holdup measurements from dual-energy flow meter 314.

Another method for adjusting the values of the water-related end-points of the nuclear density and gas-water-oil holdup measurement is as follows: It is assumed that the water flowing through the device is a mixture of two known waters, for example formation water and injected water. It is further assumed that the conductivities of these two waters, and their nuclear calibration parameters $\mu_1$ and $\mu_2$ (for example, mass attenuations $\mu_{NaCl}$ and $\mu_{CaCl2}$) have been determined beforehand, for example by water analysis 302 on previously collected samples. At any instant, t, the current values of each calibration parameter are estimated as a linear combination of the corresponding parameters for the two known waters, the combination being a linear combination in the same proportion as the conductivities:

$$\mu(t) = [(\sigma(t) - \sigma_2)^* \mu_2 + (\sigma_1 - \sigma(t))^* \mu_2]/[\sigma_1 - \sigma_2] \quad (9)$$

where $\mu(t)$ denotes the current value of the calibration parameter, $\sigma(t)$ the current conductivity, $\mu_i$ and $\sigma_i$ the calibration values and conductivity of the two endpoint waters (where i=1,2).

This approach is simple to implement, and requires no assumption be made about the chemical composition of the flowing brine. However, it requires that characterised samples be available. In addition, it is strictly valid only for small temporal variations in conductivity, since it is based on the assumption of a linear relationship between conductivity change and end-point change. Whilst valid for small changes, the relationship is non-linear for large changes.

Monitoring changes in water salinity on-line, under multiphase flow conditions, is extremely beneficial, especially for permanent (e.g. subsea) metering applications. A good example is illustrated in a paper by Marathon UK describing the application and 'benefits of Framo's subsea dual energy multiphase flowmeter on West Brae Field (located 160 miles northeast of Aberdeen, Scotland in 350 feet of water in the North Sea). See, Larson T A: "Operational experience and utilization of the data from the subsea multiphase flowmeter in the west Brae field", North Sea Flow Measurement Workshop, October 2000, Gleneagles, Scotland. The salinity of the seawater injected in the reservoir is about half of the reservoir water. Injected water may eventually breakthrough in some of the producing wells (in 6 years, estimated by reservoir simulation). The reduction of the effective salinity of the water metered will result in an underestimation of the water cut by 5% (at 80% to 90% actual water cut) by the multiphase flowmeter if not corrected for. The recommended practice is to manually update the flowmeter water salinity information once a year, obtained from commingled water sample analysis. It is clear that, on-line monitoring of water salinity change will provide continuous update of the flowmeter calibration.

According to the invention, there are a number of other uses of on-line water conductivity (salinity) measurement of multiphase mixtures for down-hole applications. Following are some examples.

1. The microwave open-coaxial probe can be used as a standalone salinity (and water-cut) meter, suitable for permanent monitoring and for produced water management (e.g. for discriminating 'good' and 'bad' waters, detecting sweep water breakthrough, for managing the deployment of a down-hole water/oil separator).

2. The Electromagnetic Propagation Tool (EPT) gives estimate water saturation of the invaded zone of a formation by interpreting the transmitting microwave attenuation and propagation time (mainly a function of receivers' phase-shift) through the zone. The interpretation of water saturation based on a permittivity mixing law (of the rock matrix and the pore fluids) can be made more robust when using the fundamental parameters of the zone permittivity and/or conductivity, both being a function of the measured attenuation and phase shift. See, Ellis D V: "Well Logging for Earth Scientists", Elsevier Science Publishing Co. 1987, Chapter 7. By interpreting these two parameters in a similar way as described herein, water salinity in the invaded zone can also be obtained, thereby providing a salinity-independent water saturation interpretation (the effect of a mudcake has to be considered, given its thickness and complex permittivity).

3. On-line fluid resistivity (conductivity) measurement in the Schlumberger Modular Formation Dynamics Tester (MDT) tool flowline helps to discriminate filtrate from water-base muds and formation fluids. Most of the time, an Optical Fluid Analyzer (OFA), a visible and near-infrared absorption spectrometer) is used to measure water-oil fraction in the MDT flowline. The present MDT resistivity probe consists of five ring electrodes (two for voltage detection, two for current injection and one as guard). The probe saturates at about 24 ohm-m for a hydrocarbon-continuous mixture even if the water fraction is relatively high. This resistivity measurement, when performed during fluid sampling, can potentially fail to detect (water-free) hydrocarbon fluid, and thus the subsequent dumping of formation fluid until an uncontaminated sample is obtained. By using a microwave probe, the water fraction of both hydrocarbon and water continuous fluids can be estimated from mixture permittivity and/or mixture conductivity measurement, independent of water salinity (on-line water conductivity can be measured under multiphase conditions in the MDT flowline). This improves the tool efficiency and robustness in discriminating between formation fluids and filtrate from water-base muds, and the quality of an uncontaminated hydrocarbon sample. Combined with chemical sensing elements for water pH and dominant ion species, a single microwave on-line water conductivity probe can provide the additional information for the full characterization of formation water. Monitoring filtrate clean up for oil-based mud (OBM) when sampling oil can be provided in cases where there is sufficient complex-permittivity contrast between the OBM and oil.

4. On-line water conductivity measurement of drilling fluids can yield information of changes in the fluid chemistry. Conventional sensors are not capable of monitoring water sampling in wells drilled with water-based mud (WBM); a real-time flowline sensor in the MDT will be desirable to achieve this; the MDT resistivity cell normally has insufficient resolution. By using microwave sensors, water sampling in wells drilled with WBM can be better monitored by measuring mixture permittivity, mixture conductivity and water conductivity at the same time, and in real-time.

While preferred embodiments of the invention have been described, the descriptions are merely illustrative and are not intended to limit the present invention.

What is claimed is:

1. A method of estimating water conductivity in a multiphase mixture of water and other substances comprising the steps of:

obtaining values representing the mixture permittivity and mixture conductivity of the multiphase mixture;

obtaining a relationship between water conductivity and water permittivity; and estimating water conductivity of the multiphase mixture using at least the values representing mixture permittivity, mixture conductivity, and the relationship between water conductivity and water permittivity, wherein when the mixture is substantially water continuous, the ratio of the mixture conductivity to the mixture permittivity is assumed to be approximately eaual to the ratio of water conductivity to water permittivity, wherein when the mixture is substantially oil continuous, a trend of the ratio of the mixture conductivity to the mixture permittivity is matched with a theoretical prediction of the ratio for a given water conductivity, and wherein when the mixture is intermittently oil and water continuous, the ratio of values representing water-rich segments of mixture conductivity to mixture permittivity is assumed to be approximately equal to the ratio of water conductivity to water permittivity.

2. The method of claim 1 wherein the theoretical prediction is based on a relationship of mixture permittivity as a function of water fraction, water permittivity, water conductivity and frequency, and a relationship of mixture conductivity as a function of water fraction, water permittivity, water conductivity and frequency.

3. The method of claim 1 wherein the relationship between water conductivity and water permittivity is obtained from known published empirical correlations.

4. The method of claim 3 wherein the known published correlations are of water conductivity and permittivity as a function of salinity, salt species, temperature and pressure, and frequency.

5. The method of claim 1 wherein the relationship between water conductivity and water permittivity is obtained by derivation based on measured values.

6. The method of claim 1 wherein the mixture permittivity and mixture conductivity are obtained using reflection measurements from an open-ended coaxial probe exposed to the multiphase mixture.

7. The method of claim 6 wherein the open-ended coaxial probe is exposed to the multiphase mixture in a hazardous area Zone 0.

8. The method of claim 1 wherein the mixture permittivity and mixture conductivity are obtained using transmission measurements using at least one transmitter antenna and one receiver antenna to interrogate the multiphase mixture.

9. The method of claim 1 wherein the mixture permittivity and mixture conductivity are obtained using resonance measurements from one or more antennae.

10. The method of claim 1 further comprising the step of monitoring changes in water salinity in the multiphase mixture using the estimated water conductivity.

11. The method of claim 10 wherein the step of monitoring comprises generating a correction to brine low-energy mass attenuation.

12. The method of claim 1 further comprising the step of measuring the mixture permittivity and mixture conductivity using a coaxial probe permanently installed in a wellbore.

13. The method of claim 1 further comprising the step of measuring the mixture permittivity and mixture conductivity using a coaxial probe installed on a pipe wall.

14. The method of claim 1 further comprising the step of combining the estimated water conductivity of the multiphase mixture with measurements from an electromagnetic propagation tool to provide a salinity-independent water saturation estimate of an invaded zone of a subterranean formation.

15. The method of claim 1 further comprising the steps of:
measuring the mixture permittivity and mixture conductivity using a coaxial probe installed in a flowline of a downhole fluid sampling tool;
discriminating formation fluids from filtrate based on the estimated water conductivity, the mixture permittivity and mixture conductivity.

16. The method of claim 1 further comprising the step of measuring the mixture permittivity and mixture conductivity using a coaxial probe installed in a wellbore drilled with water based mud.

17. The method of claim 1 further comprising correcting for salinity change for a dual energy flow meter using the estimated water conductivity.

18. The method of claim 1 wherein the mixture permittivity and mixture conductivity are obtained using measurements from an open-ended microwave coaxial probe.

19. The method of claim 18 wherein the microwave probe operates at approximately 2 GHz.

20. An apparatus for estimating water conductivity in a multiphase mixture of water and other substances comprising:
one or more sensors for measuring mixture permittivity and mixture conductivity of the multiphase mixture; and
a processor adapted to estimate water conductivity by combining the measured mixture permittivity and mixture conductivity with an obtained relationship between water conductivity and water permittivity, wherein when the mixture is substantially water continuous, the processor assumes that the ratio of the mixture conductivity to the mixture permittivity is approximately eaual to the ratio of water conductivity to water permittivity, and wherein when the mixture is substantially oil continuous, the processor matches a trend of the ratio of the mixture conductivity to the mixture permittivity with a theoretical prediction of the ratio for a given water conductivity, and wherein when the mixture is intermittently oil and water continuous, the processor assumes that the ratio of values representing water-rich segments of mixture conductivity to mixture permittivity to be approximately equal to the ratio of water conductivity to water permittivity.

21. The apparatus of claim 20 wherein the one or more sensors are microwave sensors.

22. The apparatus of claim 21 wherein the one or more sensors operate at approximately 2 GHz.

23. The apparatus of claim 20 wherein the theoretical prediction is based on a relationship of mixture permittivity as a function of water fraction, water permittivity, water conductivity and frequency, and a relationship of mixture conductivity as a function of water fraction, water permittivity, water conductivity and frequency.

24. The apparatus of claim 20 wherein the relationship between water conductivity and water permittivity is obtained from known published empirical correlations.

25. The apparatus of claim 24 wherein the known published correlations are of water conductivity and permittivity as a function of salinity, salt species, temperature and pressure, and frequency.

26. The apparatus of claim 20 wherein the relationship between water conductivity and water permittivity is obtained by derivation based on measured values.

27. The apparatus of claim 20 wherein the one or more sensors comprise a coaxial probe exposed to the multiphase mixture and use reflection measurements from the coaxial probe.

28. The apparatus of claim 20 wherein the one or more sensors comprise at least one transmitter and one receiver to interrogate the multiphase mixture, and the mixture permittivity and mixture conductivity are obtained using transmission measurements.

29. The apparatus of claim 20 wherein the one or more sensors comprise one or more antennae and the mixture permittivity and mixture conductivity are measured using resonance measurements from the one or more antennae.

30. The apparatus of claim 20 wherein the processor monitors changes in water salinity in the multiphase mixture using the estimated water conductivity.

31. The apparatus of claim 30 wherein the processor performs the monitoring by generating a correction to brine low-energy mass attenuation.

32. The apparatus of claim 20 wherein the one or more sensors comprises a coaxial probe permanently installed in a wellbore.

33. The apparatus of claim 20 wherein the processor combines estimated water conductivity of the multiphase mixture with measurements from an electromagnetic propagation tool to provide a salinity-independent water saturation estimate of an invaded zone of a subterranean formation.

34. The apparatus of claim 20 wherein the one or more sensors comprise a coaxial probe installed in a flowline of a downhole fluid sampling tool, and the processor discriminates formation fluids from filtrate based on the estimated water conductivity.

35. The apparatus of claim 20 further comprising a dual energy flow meter that uses the estimated water conductivity to correct for variations in salinity level.

* * * * *